US012735337B2

(12) United States Patent
Shimamoto et al.

(10) Patent No.: US 12,735,337 B2
(45) Date of Patent: Sep. 15, 2026

(54) METHOD FOR TREATING WASTEWATER

(71) Applicant: Mitsubishi Chemical Corporation, Tokyo (JP)

(72) Inventors: Akihiro Shimamoto, Tokyo (JP); Yasuhito Yamamoto, Tokyo (JP); Shuichi Yunomura, Tokyo (JP); Takatoshi Kimura, Tokyo (JP); Michiru Kamizono, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 637 days.

(21) Appl. No.: 17/950,769

(22) Filed: Sep. 22, 2022

(65) Prior Publication Data

US 2023/0093040 A1 Mar. 23, 2023

Related U.S. Application Data

(63) Continuation of application No. PCT/JP2021/011832, filed on Mar. 23, 2021.

(30) Foreign Application Priority Data

Mar. 24, 2020 (JP) ................................ 2020-052011
Mar. 1, 2021 (JP) ................................ 2021-031309

(51) Int. Cl.
*C02F 3/34* (2023.01)
*C02F 1/00* (2023.01)
(Continued)

(52) U.S. Cl.
CPC ................. *C02F 3/34* (2013.01); *C02F 1/00* (2013.01); *C02F 1/28* (2013.01); *C02F 1/44* (2013.01);
(Continued)

(58) Field of Classification Search
CPC ...... C02F 3/34; C02F 1/00; C02F 1/28; C02F 1/44; C02F 1/72; C02F 1/283;
(Continued)

(56) References Cited

U.S. PATENT DOCUMENTS 4,302,542 A * 11/1981 Hitzman ................. C12N 1/32 435/99
5,139,792 A * 8/1992 Ware ................... A61K 35/747 426/807
(Continued)

FOREIGN PATENT DOCUMENTS

CN 101845408 A 9/2010
CN 103571774 A 2/2014
(Continued)

OTHER PUBLICATIONS

P. Wang, et al., Screening Microorganisms for Utilization of Furfural and Possible Intermediates in Its Degradative Pathway, Biotechnology Letters, vol. 16 No .9 (Sep. 1994) p. 977-982 (Year: 1994).*
(Continued)

*Primary Examiner* — Fred Prince
(74) *Attorney, Agent, or Firm* — Morgan, Lewis & Bockius LLP

(57) ABSTRACT

The present invention relates to a method for treating wastewater containing a furan compound, a microbial preparation for use in the method, a method for high density culture of a microorganism for use in the above method, and a method for producing a microbial preparation by using the culture method.

12 Claims, 4 Drawing Sheets

(51) Int. Cl.

| | |
|---|---|
| ***C02F 1/20*** | (2023.01) |
| ***C02F 1/28*** | (2023.01) |
| ***C02F 1/44*** | (2023.01) |
| ***C02F 1/72*** | (2023.01) |
| ***C02F 3/12*** | (2023.01) |
| ***C12N 1/20*** | (2006.01) |
| ***C12P 17/04*** | (2006.01) |
| *C02F 101/36* | (2006.01) |
| *C02F 103/36* | (2006.01) |

(52) U.S. Cl.
CPC .................. *C02F 1/72* (2013.01); *C12N 1/20* (2013.01); *C12P 17/04* (2013.01); *C02F 1/283* (2013.01); *C02F 1/444* (2013.01); *C02F 3/1268* (2013.01); *C02F 3/341* (2013.01); *C02F 3/342* (2013.01); *C02F 2101/366* (2013.01); *C02F 2103/365* (2013.01); *C02F 2209/08* (2013.01); *C02F 2303/04* (2013.01); *C02F 2305/026* (2013.01); *Y02W 10/10* (2015.05)

(58) Field of Classification Search
CPC ........ C02F 1/444; C02F 3/1268; C02F 3/341; C02F 3/342; C02F 2101/366; C02F 2103/365; C02F 2209/08; C02F 2303/04; C02F 2305/026; C12N 1/20; C12P 17/04; Y02W 10/10
USPC .......................................... 210/606, 610, 611
See application file for complete search history.

(56) References Cited

U.S. PATENT DOCUMENTS

| | | | | |
|---|---|---|---|---|
| 5,622,819 | A * | 4/1997 | Herman | C12M 33/12 435/243 |
| 6,803,220 | B2 * | 10/2004 | Yano | C12P 7/625 435/71.1 |
| 11,034,986 | B1 * | 6/2021 | Li | C12P 17/04 |
| 2003/0044966 | A1 * | 3/2003 | Perriello | C02F 3/34 435/262.5 |
| 2012/0039853 | A1 * | 2/2012 | Corveleyn | A23L 33/135 435/253.4 |
| 2012/0122164 | A1 * | 5/2012 | El-Shafie | C12N 1/06 423/437.1 |
| 2013/0337518 | A1 * | 12/2013 | Razavi-Shirazi | C12P 7/46 435/141 |
| 2016/0145651 | A1 | 5/2016 | Kurihara et al. | |
| 2016/0186226 | A1 * | 6/2016 | Han | C12P 21/00 435/71.2 |
| 2016/0230198 | A1 * | 8/2016 | Vemuri | C12N 9/93 |
| 2016/0355829 | A1 * | 12/2016 | Schröder | C07K 14/245 |
| 2017/0137846 | A1 * | 5/2017 | Atsumi | C12Y 103/01038 |
| 2018/0103671 | A1 * | 4/2018 | Hernandez-Brenes | A61K 45/06 |
| 2019/0062693 | A1 | 2/2019 | Ito et al. | |
| 2019/0071337 | A1 * | 3/2019 | Razavi-Shirazi | C12P 39/00 |
| 2019/0247447 | A1 * | 8/2019 | Button | A61K 35/742 |
| 2020/0337314 | A1 * | 10/2020 | Wood | C05G 5/23 |
| 2022/0017911 | A1 * | 1/2022 | Temme | C12Q 1/02 |

FOREIGN PATENT DOCUMENTS

| | | | | |
|---|---|---|---|---|
| CN | 105668807 | A * | 6/2016 | C02F 3/34 |
| CN | 105802874 | A | 7/2016 | |
| CN | 107365724 | A | 11/2017 | |
| EP | 0567102 | A2 | 10/1993 | |
| JP | H04-234981 | A | 8/1992 | |
| JP | H06-046869 | A | 2/1994 | |
| JP | H06-055153 | A | 3/1994 | |
| JP | H09-085283 | A | 3/1997 | |
| JP | H09-098793 | A | 4/1997 | |
| JP | 09191893 | A * | 7/1997 | |
| JP | H09-224664 | A | 9/1997 | |
| JP | 2002-000753 | A | 1/2002 | |
| JP | 2016-067288 | A | 5/2016 | |
| JP | 2017-042097 | A | 3/2017 | |
| JP | 2018-126085 | A | 8/2018 | |
| JP | 2019-030292 | A | 2/2019 | |
| WO | WO-2009145840 | A * | 12/2009 | C12N 9/16 |
| WO | WO-2011158975 | A * | 12/2011 | C12N 15/52 |
| WO | 2015/005307 | A1 | 1/2015 | |
| WO | 2017/073752 | A1 | 5/2017 | |

OTHER PUBLICATIONS

N. Nichols, et al., Chemotaxis to Furan Compounds by Furan-Degrading Pseudomonas Strains, Applied and Environmental Microbiology, Sep. 2012, vol. 78 No. 17 p. 6365-6368 (Year: 2012).*

Koopman et al., Identification and characterization of the furfural and 5-(hydroxymethyl)furfural degradation pathways of Cupriavidus basilensis HMF14. Proc Natl Acad Sci U S A. Mar. 16, 2010;107(11):4919-24 (Year: 2010).*

Wierckx et al., Microbial degradation of furanic compounds: biochemistry, genetics, and impact, Appl Microbiol Biotechnol (2011) 92:1095-1105 (Year: 2011).*

Tamaoka et al., Reclassification of Pseudomonas acidovorans den Dooren de Jong 1926 and Ps. testosteroni Marcus and Talalay 1956 as Comamonas acidovorans comb. nov. and Comamonas testosteroni comb. nov., with an Emended Description of the Genus Comamonas, Intl. J Syst. and Evol. Microbio, 37(1) 1987 (Year: 1987).*

Machine-generated English translation of CN 10668807, generated on Oct. 6, 2025.*

Bako et al., Biodegradation of PCB congeners by Paraburkholderia xenovorans LB400 in presence and absence of sediment during lab bioreactor experiments, Environmental Pollution 271 (2021) 116364, pp. 1-10.*

Wierckx et al., "Microbial degradation of furanic compounds: biochemistry, genetics, and impact," Applied Microbiology Biotechnology, 92: 1095-1105 (2011).

Terasawa, "Isolation of a Microbe Converting 5-Hydroxymethylfurfural into 5-Hydroxymethyl-2-furancarboxylic Acid," Bullentin of the Faculty of Education, Kanazawa University, 46: 1-8 (1997)(see English abstract).

Guarnieri et al., "Conversion and assimilation of furfural and 5-(hydroxymethyl)furfural by Pseudomonas putida KT2440," Metabolic Engineering Communications, 4: 22-28 (2017).

Yang et al., "Biotransformation of 5-hydroxy-methylfurfural into 2,5-furan-dicarboxylic acid by bacterial isolate using thermal acid algal hydrolysate," Bioresource Technology, 214: 311-318 (2016).

Zhang et al., "Efficient synthesis of 5-hydroxymethyl-2-furancarboxylic acid by *Escherichia coli* overexpressing aldehyde dehydrogenases," Journal of Biotechnology, 307: 125-130 (2020).

Dietrich et al., "Model Study to Assess Softwood Hemicellulose Hydrolysates as the Carbon Source for PHB Production in Paraburkholderia sacchari IPT 101," Biomacromolecules, 19: 188-200 (2018).

International Search Report issued in corresponding International Patent Application No. PCT/JP2021/011832 dated Jun. 1, 2021.

Office Action issued in corresponding Japanese Patent Application No. 2022-510514, dated Jan. 21, 2025.

Office Action issued Feb. 9, 2024 for Chinese Patent Application No. 202180024079.X.

Khudhair, et al., "New application of single and mixed immobilized cells for furfural biodegradation," 2019, Bioremediation Journal, vol. 23, Issue No. 1, p. 32-41 (https://doi.org./10.1080/10889868.2019.1569585).

Office Action issued in corresponding Japanese Patent Application No. 2022-510514, dated Jun. 10, 2025.

* cited by examiner

METHOD FOR TREATING WASTEWATER

TECHNICAL FIELD

Related Applications

The specification claims the priorities Japanese Patent Application No. 2020-052011 (filed on Mar. 24, 2020) and Japanese Patent Application No. 2021-031309 (filed on Mar. 1, 2021), the contents of which are incorporated herein by reference.

Technical Field

The present invention relates to a method for treating wastewater containing a furan compound, a microbial preparation for use in the method, a method for high density culture of a microorganism for use in the above method, and a method for producing a microbial preparation by using the culture method.

BACKGROUND ART

A furan compound refers to a cyclic ether compound represented by furfural, 2-methylfuran, 3-methylfuran, furan, dihydrofuran, furfuryl alcohol, tetrahydrofuran, tetrahydrofurfuryl alcohol and hydroxymethylfurfural, which are useful petrochemical derivatives. Until now, furan compounds have been produced from petroleum; however, with a growing concern about environmental issues in recent years, producing furan compounds from biomass resources (as raw materials) has been studied.

Wastewater from facilities for producing furan compounds contains furan-aldehydes such as furfural and tetrahydrofurfural. Of the furan compounds, in particular, a furan-aldehyde is known to inhibit proliferation and metabolism of microorganisms and have a high toxicity to activated sludge. Because of this, it is difficult to biologically treat a furan-aldehyde. Since the values defined by wastewater regulations are strict in many countries, it has been required to develop a technique efficiently treating wastewater containing furan compounds.

Recently, microorganisms specifically degrading furan compounds have been found and biological methods for treating furan compounds using the microorganisms have been reported (Patent Literatures 1 and 2, Non Patent Literature 1).

Patent Literature 1 discloses a method for degrading hydroxymethylfurfural and furfural by a fungus, *Paecilomyces* sp. FA13 strain. However, use of this method is limited to production of compost. In addition, in view of environmental burden and energy cost, this method is unsuitable for treating wastewater containing a large amount of furan compounds. Patent Literature 2 discloses a method for degrading a cyclic ether compound including furan by using *Pseudonocardia* sp. RM31 strain. This method is effective for reducing the amount of 1,4-dioxane in wastewater but not for furan compounds.

Microorganisms are used for not only treating wastewater but also attaining various purposes, at present. For example, enzymes produced by microorganisms are used for producing compounds and microorganisms are added in soil after crop harvest, as a soil conditioner.

For these applications, a large amount of microorganisms are required in some situations. Thus, a technique for culturing microorganisms at a high density (high concentration) is desired (see, Patent Literatures 3, 4).

CITATION LIST

Patent Literature

Patent Literature 1: Japanese Patent Laid-Open No. 2016-67288

Patent Literature 2: Japanese Patent Laid-Open No. 2017-42097

Patent Literature 3: Japanese Patent Laid-Open No. 2019-30292

Patent Literature 4: Japanese Patent Laid-Open No. H4-234981

Non Patent Literature

Non Patent Literature 1: Wierckx et al., Appl Microbiol Biotechnol (2011) 92: 1095-1105

SUMMARY OF INVENTION

Technical Problem

A first object of the present invention is to provide a novel method for efficiently treating wastewater containing a furan compound. A second object of the present invention is to provide a technique for culturing a microorganism at a high concentration in order to obtain a large amount of a microorganism to be used in, e.g., wastewater treatment.

Solution to Problem

The present inventors conducted intensive studies in consideration of problems with the conventional technology, and as a result, they have found that in a biological treatment of wastewater containing a furan compound, the wastewater is contacted with a microorganism having hydroxymethylfurfural and/or furfural oxidase activity for degradation, so that the wastewater can be efficiently treated while preventing reduction in activity of e.g., activated sludge. Based on the finding, the present invention has been accomplished.

More specifically, the present invention provides the following [1] to [21].

[1]A microbial preparation for treating wastewater containing a furan compound, the microbial preparation comprising at least one selected from a microorganism belonging to the genus *Comamonas*, a microorganism belonging to the genus *Burkholderia*, a microorganism belonging to the genus *Paraburkholderia* and a microorganism belonging to the genus *Pseudomonas*.

[2] The microbial preparation according to [1], wherein the microorganism belonging to the genus *Comamonas* is *Comamonas testosteroni* and/or *Comamonas thiooxydans*; the microorganism belonging to the genus *Burkholderia* is *Burkholderia multivorans*; the microorganism belonging to the genus *Paraburkholderia* is *Paraburkholderia xenovorans*; and the microorganism belonging to the genus *Pseudomonas* is *Pseudomonas putida* or *Pseudomonas oryzihabitans*.

[3] The microbial preparation according to [1] or [2], wherein the furan compound is a furan-aldehyde.

[4]A method for treating wastewater, comprising a step of contacting wastewater containing a furan compound with at least one selected from a microorganism belonging to the genus *Comamonas*, a microorganism belonging to the genus *Burkholderia*, a microorganism belonging to the genus *Paraburkholderia* and a microorganism belonging to the genus *Pseudomonas*.

[5] The method for treating wastewater according to [4], wherein the microorganism belonging to the genus *Comamonas* is *Comamonas testosteroni* and/or *Comamonas thiooxydans*; the microorganism belonging to the genus *Burkholderia* is *Burkholderia multivorans*; the microorganism belonging to the genus *Paraburkholderia* is *Paraburkholderia xenovorans*; the microorganism belonging to the genus *Pseudomonas* is *Pseudomonas putida* or *Pseudomonas oryzihabitans*.

[6] The method for treating wastewater according to [4] or [5], wherein the furan compound is a furan-aldehyde.

[7]A method for treating wastewater, comprising a step of contacting wastewater containing a furan compound with at least one selected from a microorganism belonging to the genus *Comamonas*, a microorganism belonging to the genus *Burkholderia*, a microorganism belonging to the genus *Paraburkholderia* and a microorganism belonging to the genus *Pseudomonas*, in the presence of a membrane separator.

[8]A method for treating wastewater, comprising steps of:

(1) contacting wastewater containing a furan compound with at least one selected from a microorganism belonging to the genus *Comamonas*, a microorganism belonging to the genus *Burkholderia*, a microorganism belonging to the genus *Paraburkholderia* and a microorganism belonging to the genus *Pseudomonas*; and (2) contacting wastewater obtained in step (1) with at least one selected from activated carbon, Fenton's catalyst and a polycyclic aromatic degrading enzyme.

[9] The method for treating wastewater according to any one of [4] to [8], wherein the wastewater to be obtained has a CODcr value of 500 ppm or less.

[10]A method for culturing a microorganism belonging to the genus *Comamonas*, a microorganism belonging to the genus *Burkholderia* or a microorganism belonging to the genus *Paraburkholderia*, comprising a step of culturing the microorganism in a culture medium containing gluconic acid.

[11]A method for culturing a microorganism belonging to the genus *Comamonas*, comprising a step of culturing the microorganism in a culture medium containing at least one selected from gluconic acid, ethanol and succinic acid.

[12] The method according to [10] or [11], wherein the culture medium containing a microorganism has an optical density of 15 or more at a wavelength of 660 nm, 24 hours after initiation of culture.

[13] The method according to [10] or [11], wherein the culture medium containing a microorganism has an optical density of 20 or more at a wavelength of 660 nm, 48 hours after initiation of culture.

[14] The method according to any one of [10] to [13], wherein the gluconic acid, ethanol and succinic acid present in the culture medium all have a concentration of 10 g/L or less.

[15] The method according to any one of [10] to [14], wherein the microorganism has a proliferation rate of 0.2 g/L/hr or more on a basis of dry weight of microbial cells.

[16] The method according to any one of [10] to [15], wherein the culture is carried out in accordance with feeding culture.

[17] The method according to any one of [10] to [16], comprising a step of passing a gas containing 90% (v/v) or more of oxygen through a culture solution.

[18] The method according to [17], wherein the gas is passed at an air-flow rate of 6 to 5 vvm.

[19]A method for producing the microbial preparation according to any one of [1] to [3], comprising a step of lyophilizing a composition containing a microorganism obtained by the method according to any one of [10] to [18] and a cryoprotectant in an amount 1 to 10 fold on a basis of dry weight of the microorganism.

[20] The method according to [19], wherein the cryoprotectant is at least one selected from trehalose, skim milk and glutamic acid.

[21] The microbial preparation according to any one of [1] to [3], produced by the method according to [19] or [20].

Advantageous Effects of Invention

According to the present invention, a furan compound contained in wastewater can be efficiently degraded while suppressing reduction in power of, e.g., activated sludge. According to the present invention, it is possible to degrade not only a furan compound but also other components including acid components such as formic acid and acetic acid and sugars such as xylose contained in wastewater. Further, if a treatment with activated carbon, Fenton's catalyst and a polycyclic aromatic degrading enzyme is carried out in combination after the microbial treatment, the CODcr value of the wastewater can be reduced and a treatment for wastewater satisfying strict regulations on wastewater can be realized. The present invention allows for high density culture of a microorganism belonging to the genus *Comamonas*, a microorganism belonging to the genus *Burkholderia*, or a microorganism belonging to the genus *Paraburkholderia* to be used in wastewater treatment. Owing to this, the microorganism can be obtained in a short time and in a large amount.

DESCRIPTION OF EMBODIMENTS

1. Wastewater Treatment Method

Figure 1:
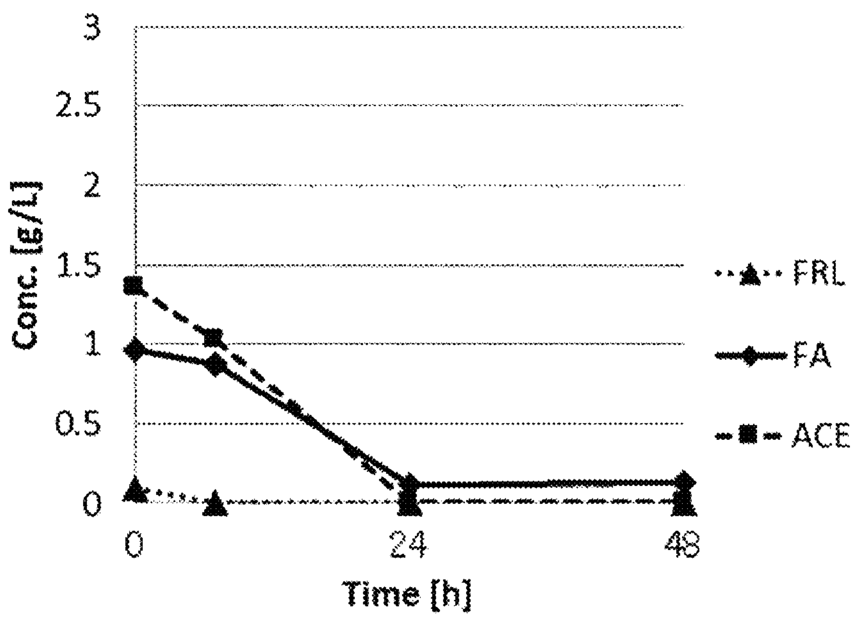
FIG. 1 The figure shows degradation of furfural, formic acid and acetic acid by *Comamonas testosteroni* NBRC12047 strain (change in concentration for over 48 hours). The vertical axis represents concentration [g/L] and the horizontal axis represents time [h] (dotted line: ▲ (FRL: furfural), solid line: ♦ (FA: formic acid), dashed line: ■ (ACE: acetic acid)).

The present invention relates to a method for biologically treating wastewater containing a furan compound characterized by contacting the wastewater with a microorganism having hydroxymethylfurfural and/or furfural oxidase activity.

(1) Wastewater to be Subjected to Treatment

In the present invention, the wastewater to be treated is wastewater containing a furan compound. The source from which wastewater is generated is not limited as long as the wastewater contains a furan compound. Examples of the wastewater include wastewater discharged from a step for producing a furan compound from a petroleum feedstock and wastewater discharged from a step for producing furfural from C5 sugar extracted from biomass (bagasse, i.e., a residue after squeezing of sugarcane).

The wastewater may contain not only a furan compound but also components including acids, such as formic acid, acetic acid and lactic acid, and sugars such as xylose. These components such as acids and sugars are also contained in wastewater discharged from a process for producing a furan compound from biomass and make it difficult to biologically treat wastewater, similarly to a furan compound. For the reason, it is preferable to remove these components (acids and sugars) from wastewater.

Wastewater may be previously treated, if necessary, prior to a microbial treatment. For example, if wastewater is rather acidic due to the content of a large amount of acid components, an alkali component may be added to adjust pH of the wastewater to be 5 to 9, preferably 5.5 to 8.5 and more preferably 6 to 8. The alkali component to be used is not limited, for example, NaOH or KOH can be used in a solid or liquid state.

(2) Furan Compound

A furan compound refers to a compound having a furan skeleton, such as furfural, hydroxymethylfurfural, 2-methylfuran, 3-methylfuran, furan, dihydrofuran, furfuryl alcohol, tetrahydrofuran and tetrahydrofurfuryl alcohol. In the present invention, the furan compound to be treated is not particularly limited. A furan-aldehyde such as furfural and tetrahydrofurfural, which is highly toxic to microorganisms and activated sludge, is a particularly desirable target to be treated (degraded).

(3) Microorganism to be Used for Wastewater Treatment

The microorganism to be used in the present invention is a "microorganism having hydroxymethylfurfural and/or furfural oxidase activity". The "hydroxymethylfurfural and/or furfural oxidase activity" refers to the activity of an enzyme which oxidizes hydroxymethylfurfural and/or furfural to convert them into the corresponding carboxylic acids. More specifically, the enzyme oxidizes hydroxymethylfurfural (also referred to as 5-hydroxymethylfurfural) to 5-formyl-2-furoic acid, and further into 2,5-furandicarboxylic acid; and oxidizes furfural to 2-furoic acid.

Degradation of hydroxymethylfurfural, in other words, oxidization of hydroxymethylfurfural to 5-formyl-2-furoic acid and further to 2,5-furandicarboxylic acid, can be checked by a means commonly known in the technical field, such as HPLC. Similarly, degradation of furfural, in other words, oxidation of furfural to 2-furoic acid, can be checked by HPLC (means commonly known in the technical field).

Examples of the microorganism include a microorganism belonging to the genus *Comamonas*, a microorganism belonging to the genus *Burkholderia*, a microorganism belonging to the genus *Paraburkholderia* and a microorganism belonging to the genus *Pseudomonas*. The microorganisms may be used alone or in combination (two or more).

As the microorganism belonging to the genus *Comamonas*, for example, *Comamonas acidovorans, Comamonas composti, Comamonas guangdongensis, Comamonas terrae, Comamonas testosteroni* and *Comamonas thiooxydans* are preferable. Of them, *Comamonas testosteroni* and *Comamonas thiooxydans* are more preferable, and *Comamonas testosteroni* is particularly preferable.

Examples of *Comamonas testosteroni* that can be used include, but are not limited to, NBRC 12047 strain, NBRC 12048 strain, NBRC 14951T strain, NBRC 100989 strain, NBRC 109938 strain, NBRC 110673 strain, ATCC 700441 strain, ATCC 13474 strain, ATCC 700441D-5 strain, ATCC 55744 strain, ATCC 49249 strain, ATCC 33083 strain, ATCC 17510 strain, ATCC 17409 strain, ATCC 15666 strain, ATCC 15667 strain, ATCC 39523 strain, ATCC 53716 strain, ATCC 25094 strain, TA441 strain and TK102 strain.

Examples of *Comamonas thiooxydans* that can be used include, but are not limited to, NBRC 110656 strain, S23 strain and CNB-1 strain.

As the microorganism belonging to the genus *Burkholderia*, for example, *Burkholderia vietnamiensis, Burkholderia lata, Burkholderia cenocepacia, Burkholderia ambifaria, Burkholderia multivorans, Burkholderia cepacia, Burkholderia dolosa, Burkholderia pyrrocinia, Burkholderia contaminans, Burkholderia ubonensis, Burkholderia diffusa, Burkholderia latens, Burkholderia territorii, Burkholderia seminalis, Burkholderia pseudomultivorans, Burkholderia metallica, Burkholderia stagnalis, Burkholderia stabilis, Burkholderia glumae, Burkholderia gladioli, Burkholderia insecticola* and *Burkholderia plantarii* are preferable. Of them, *Burkholderia multivorans* is more preferable.

Examples of *Burkholderia multivorans* that can be used include, but are not limited to, NBRC 102086 strain, ATCC 17616D-5 strain, ATCC 17616 strain and ATCC BAA-247 strain.

As the microorganism belonging to the genus *Paraburkholderia*, for example, *Paraburkholderia xenovorans, Paraburkholderia phymatum, Paraburkholderia phenoliruptrix, Paraburkholderia phenoliruptrix, Paraburkholderia phytofirmans, Paraburkholderia fungorum, Paraburkholderia caribensis, Paraburkholderia sprentiae, Paraburkholderia aromaticivorans, Paraburkholderia hospita, Paraburkholderia terrae, Paraburkholderia graminis, Paraburkholderia caledonica* and *Paraburkholderia terricola* are preferable. Of them, *Paraburkholderia xenovorans* is more preferable.

Examples of *Paraburkholderia xenovorans* that can be used include, but are not limited to, DSM 17367 strain and LB400 strain.

As the microorganism belonging to the genus *Pseudomonas*, for example, *Pseudomonas aeruginosa, Pseudomonas mendocina, Pseudomonas resinovorans, Pseudomonas alcaligenes, Pseudomonas citronellolis, Pseudomonas putida, Pseudomonas fulva, Pseudomonas monteilii, Pseudomonas soli, Pseudomonas plecoglossicida, Pseudomonas oryzihabitans, Pseudomonas syringae, Pseudomonas savastanoi, Pseudomonas amygdali, Pseudomonas cichorii, Pseudomonas avellanae, Pseudomonas protegens, Pseudomonas fluorescens, Pseudomonas poae, Pseudomonas synxantha, Pseudomonas mandelii, Pseudomonas trivialis, Pseudomonas corrugata, Pseudomonas veronii, Pseudomonas azotoformans, Pseudomonas orientalis, Pseudomonas simiae, Pseudomonas lurida, Pseudomonas entomophila, Pseudomonas stutzeri, Pseudomonas balearica, Pseudomonas brassicacearum, Pseudomonas knackmussii, Pseudomonas chlororaphis, Pseudomonas fragi, Pseudomonas lundensis, Pseudomonas alkylphenolica, Pseudomonas rhizosphaerae, Pseudomonas cremoricolorata, Pseudomonas parafulva, Pseudomonas versuta, Pseudomonas koreensis, Pseudomonas frederiksbergensis, Pseudomonas antarctica, Pseudomonas psychrotolerans, Pseudomonas silesiensis, Pseudomonas yamanorum, Pseudomonas kribbensis, Pseudomonas anguilliseptica, Pseudomonas deceptionensis, Pseudomonas denitrificans, Pseudomonas nitroreducens, Pseudomonas pavonaceae* and *Pseudomonas testosteroni* are preferable. Of them, *Pseudomonas putida* and *Pseudomonas testosteroni* are more preferable.

Examples of *Pseudomonas putida* that can be used include, but are not limited to, ATCC 3738 strain, ATCC 12653 strain, ATCC 12668 strain, ATCC 12996 strain, ATCC 13696 strain, ATCC 14164T strain, ATCC 14671 strain, ATCC 14796 strain, ATCC 15366 strain, ATCC 100650 strain, ATCC strain, ATCC 100988 strain, ATCC 101019 strain, ATCC 101020 strain, ATCC 102090 strain, ATCC 102092 strain, ATCC 102093 strain, ATCC 109109 strain, ATCC 109110 strain, ATCC 109347 strain, ATCC 109348 strain, ATCC 109349 strain, ATCC 109350 strain, ATCC 110474 strain, ATCC 110475 strain, ATCC 110476 strain, ATCC 110477 strain, ATCC 110482 strain, ATCC 110654 strain, ATCC 110666 strain and ATCC 110667 strain.

As the microorganisms, for example, microorganisms available from ATCC (American Type Culture Collection) and NBRC (NITE Biological Resource Center) can be used or microorganisms collected from, e.g., soil and wastewater, can be used; and alternatively, as the microorganisms, wild types of microorganisms or genetically modified microorganisms can be used.

(4) Method for Treating Wastewater (4-1) Microbial Treatment

Wastewater may be treated by contacting (the) wastewater and a microorganism as mentioned above with each other. As the method for contacting wastewater and a microorganism with each other, although it is not particularly limited, a microorganism may be added in wastewater or wastewater may be added to a microorganism.

A treatment (reaction) for wastewater with a microorganism may be carried out in a continuous or batch system. Those skilled in the art can appropriately select the system depending on the amount and type of wastewater.

The addition amount of a microorganism is not limited and can be appropriately set depending on, e.g., the amount and quality of wastewater to be treated. A microorganism may be added once at the time of initiation of the reaction or a plurality of times.

When a microorganism is added a plurality of times, the microorganism may be added at regular intervals or an appropriate timing while monitoring, e.g., a treatment rate of wastewater.

The time period for a treatment with a microorganism (time for allowing a microorganism and wastewater in contact with each other) is not particularly limited. The treatment can be continued until the amount of the compound to be degraded decreases to a detection limit or less.

The temperature of wastewater to be treated with a microorganism is not limited as long as the microbial treatment can be efficiently carried out. The temperature of wastewater may be, for example, 15 to 60° C., preferably 20 to 50° C., and more preferably 25 to 45° C.

The pH of the wastewater to be treated can be appropriately set in order that the microbial treatment can be efficiently carried out.

(4-2) Use of Membrane Separator

In the method for treating wastewater of the present invention, a membrane separation method may be used (in combination). The membrane separation method refers to a method of separating water (treated water) treated with a microorganism by use of separation membrane (in the presence of a membrane separator). Of the membrane separation methods, a Membrane Bio Reactor (MBR) is mentioned as a preferred embodiment of the present invention. MBR is a type of activated sludge process in which treated water and activated sludge are separated by microfiltration membrane (MF membrane) or ultrafiltration membrane (UF membrane). If wastewater is treated with a microorganism having hydroxymethylfurfural and/or furfural oxidase activity, it is possible to degrade a furan compound in wastewater while suppressing deterioration of the activated sludge, attaining efficient wastewater treatment.

In the present invention, the membrane separator may be placed in a tank for microbial treatment of wastewater or in a different tank. Membrane separation in the tank different from the microbial treatment tank can be carried out by introducing water to be treated. As the different tank, a plurality of tanks may be provided. If a microbial treatment is carried out in the presence of a membrane separator, the efficiency of the microbial reaction can be improved. As a result, the amount of a microorganism required for wastewater treatment and treatment (reaction) time can be reduced.

The type and size of the membrane separator to be used in the present invention are not particularly limited and can be appropriately selected depending on, e.g., the size of a wastewater treatment facility and the volume of wastewater.

As the type of separation membrane to be used in a membrane separator, a microfiltration membrane (MF membrane) or an ultrafiltration membrane (UF membrane) is preferable.

Examples of separation membranes, if classified by shape, include a hollow fiber membrane, a flat membrane, a tubular membrane and a sack-like membrane. Of them, a hollow fiber membrane is preferred because it is possible to accumulate a large amount of substances per area of the membrane if comparison is made on a basis of volume.

Examples of the material for a separation membrane include organic materials (e.g., cellulose, acetyl cellulose, polyolefin such as polyethylene and polypropylene, aromatic polyamide, polysulfone, polyvinyl alcohol, polymethyl methacrylate, polyvinylidene fluoride, polytetrafluoroethylene, polyacrylonitrile, polycarbonate and polytetrafluoroethylene), a metal (e.g., stainless steel) and inorganic materials (e.g., ceramic). The material for the separation membrane is appropriately selected in accordance with the properties of wastewater.

The pore size of a separation membrane may be appropriately selected in accordance with the purpose of a treatment. In the Membrane Bio Reactor (MBR) described later, the pose size of the separation membrane is usually preferably 0.001 to 3 m. If the pore size is less than 0.001 m, the resistance of the membrane is likely to be high. If the pore size is beyond 3 m, sludge cannot be completely separated, with the result that the quality of treated water (permeate) may deteriorate. The pose size of a separation membrane is more preferably within the range (of the pose-size) of a microfiltration membrane, i.e., 0.04 to 1.0 km.

In the present invention, a membrane separator may be a separator made of a commercially available separation membrane or a commercially available membrane separator. For example, a module using a hollow fiber membrane, SADF (trademark name "Sterapore SADF(™)") manufactured by Mitsubishi Chemical Corporation and a device DiaFellow(™) AM (manufactured by Mitsubishi Chemical Corporation) for a Membrane Bio Reactor, can be used. In the method for treating wastewater of the present invention, a single or a plurality of membrane separators may be disposed in a wastewater treatment facility.

When a membrane separator is used, the aeration volume is not particularly limited and can be appropriately selected depending on the amount and quality of wastewater, and the type of microorganism to be used.

(4-3) Primary Treatment

In the present invention, a treatment for removing solid substances from wastewater (hereinafter referred to as the "primary treatment") can be carried out before the microbial treatment. For example, a treatment (screening) for removing e.g., large debris, by a mesh or a bar, a treatment for removing sand by precipitating it in a settling pond and a treatment for removing mad by precipitating it in a primary setting pond, may be mentioned.

(4-4) Secondary Treatment

In the present invention, a treatment for removing organic substances (hereinafter referred to as the "secondary treatment") in wastewater by microorganisms in, e.g., activated sludge, can be carried out.

(4-5) Tertiary Treatment

In the present invention, if there are compounds not removed by a microbial treatment, a further treatment (hereinafter referred to as the "tertiary treatment") can be carried out for removing the compounds after the microbial treatment. If the tertiary treatment is used in combination, the quality of wastewater can be increased and the CODcr value (described later) can be further reduced.

The type of tertiary treatment is not particularly limited and can be appropriately selected depending on, e.g., the type of wastewater and the types of compounds not removed by a microbial treatment. For example, a treatment with activated carbon, a treatment with Fenton's catalyst and a treatment with a polycyclic aromatic oxidation catalyst can be mentioned.

(4-3-1) Treatment with Activated Carbon

Activated carbon can remove compounds that cannot be removed by a microbial treatment from wastewater by adsorption. As the activated carbon to be used, a mineral material such as petroleum pitch, coal and coke; and a material obtained from plant materials such as fruit husk including wood and coconut shells by carbonizing (heat treatment) or heat treatment followed by activation, are preferable. A commercially available activated carbon used for a liquid phase can be used.

The treatment method by activated carbon is not particularly limited. For example, a tubular container such as a column is charged with activated carbon. Then, the wastewater to be treated is supplied (passed through) to the container (activated carbon adsorption tower), and as a result, a treatment by activated carbon can be carried out. The space velocity (SV) of water to be passed through the activated carbon adsorption tower is not particularly limited and SV can be appropriately determined depending on, for example, the adsorption affinity and adsorption amounts of components contained in wastewater to activated carbon, desired water quality of treated water and wastewater quality value. For example, in the case where activated carbon rarely adsorb components (adsorption amount is low) or the case where requirement for water quality of wastewater is strict, the time of contact between the water (wastewater) to be treated and activated carbon may be increased by reducing SV.

(4-3-2) Treatment with Fenton's Catalyst

A reaction of hydrogen peroxide with a ferrous ion (iron catalyst) to generate a hydroxy radical is called as Fenton reaction. The hydroxy radicals have a strong oxidizing power, and degradation and sterilization of harmful substances and persistent pollution substances can be carried out by using the oxidizing power. The Fenton's catalyst is an iron catalyst used in the Fenton reaction. The Fenton's catalyst can be used for degrading compounds that cannot be treated with microorganisms, with hydroxy radicals, to remove the compounds from the wastewater.

The iron catalyst serving as Fenton's catalyst is not particularly limited as long as it is dissolved in water to generate ferrous ions. For example, a ferrous salt or a ferrous iron oxide is preferable. Of them, iron sulfate or iron chloride is (more) preferable because it is not necessary to control it so as to meet discharge standards and has an excellent solubility.

A treatment method using Fenton's catalyst is not particularly limited as long as a target compound can be degraded. For example, an iron reagent is added in the wastewater to be treated, if necessary, while stirring the wastewater, and thereafter, hydrogen peroxide is added to react it. The addition amounts of the iron reagent and hydrogen peroxide, the reaction time after two components are added, can be appropriately selected depending on, e.g., the types of compounds contained in the wastewater to be treated and the amount of the wastewater.

(4-3-3) Treatment with Polycyclic Aromatic Degrading Enzyme

The polycyclic aromatic degrading enzyme degrades persistent polycyclic aromatics that cannot be treated with microorganisms and removes them from wastewater. The type of polycyclic aromatic degrading enzyme, although it is not particularly limited, is preferably a polycyclic aromatic degrading enzyme having a catalytic activity to oxidize or polymerize a persistent polycyclic aromatic such as humin in the presence of hydrogen peroxide. Examples of the polycyclic aromatic degrading enzyme include peroxidase and laccase.

As the peroxidase, a peroxidase derived from Brassicaceae horseradish (*Armorica rusticana*) is suitably used. As the laccase, laccase derived from e.g., *Trametes versicolor, Rhus vernicifera, Agaricus bisporus*, or *Aspergillus* sp. is suitably used.

The treatment method with a polycyclic aromatic degrading enzyme is not limited. The enzyme may be added to the wastewater to be treated or may be immobilized on a single body and put in use. The addition amount of the polycyclic aromatic degrading enzyme to wastewater is appropriately set depending on the type or amount of wastewater. The addition amount is, for example, 0.1 to 300 ppm, preferably 0.5 to 200 ppm and more preferably 1 to 100 ppm. The treatment time with a polycyclic aromatic degrading enzyme is not particularly limited and appropriately set depending on, e.g., the amount and quality of wastewater, and type and quality of the enzyme to be used.

(5) Wastewater Obtained in the Present Invention

According to the present invention, a furan compound contained in wastewater can be efficiently degraded. Not only a furan compound but also components including acids such as formic acid and acetic acid and sugars such as xylose, can be efficiently degraded.

In addition, the wastewater after treatment with microorganisms is further treated with, e.g., activated carbon, Fenton's catalyst or a polycyclic aromatic degrading enzyme (tertiary treatment), and this allows to remove substances that cannot be removed by a microbial treatment to obtain higher-quality wastewater.

As an indicator for water quality, COD (chemical oxygen demand) and BOD (biological oxygen demand) are commonly used. COD represents the amount of oxygen required for oxidizing the amount of oxidizable substances in water; whereas, BOD represents the amount of oxygen required for oxidizing biodegradable organic substances (alone). COD varies depending on the measurement method and includes $COD_{cr}$ measured by use of potassium dichromate as an oxidizing agent; $COD_{Mn}$ measured by use of potassium permanganate as an oxidizing agent; and $COD_{OH}$ measured by use of alkaline potassium permanganate.

In the wastewater obtained by treating wastewater by the method of the present invention, not only furan compounds but also components such as acids such as formic acid and acetic acid and sugars such as xylose have been degraded. Thus, the wastewater (treated water) having high quality in light of the regulations for wastewater can be obtained. The wastewater obtained by the method of the present invention has a $COD_{cr}$ value of 500 ppm, preferably less than 120 ppm, which satisfy strict regulations on wastewater.

2. Microbial Preparation for Wastewater Treatment

The present invention provides a microbial preparation for use in a wastewater treatment method as mentioned above. Although a target furan compound is not particularly limited, for example, furan-aldehydes such as furfural and tetrahydrofurfural, highly toxic to microorganisms and activated sludge, are particularly desirable as a treatment (degradation) target.

A microbial preparation of the present invention may be a liquid (suspension) or a solid. When the microbial preparation is used in a liquid state, a microorganism cultured up to a desired density may be directly used or a mixture prepared by adding additives such as a preservative and a stabilizer to the cultured microorganism may be used as a microbial preparation. Alternatively, a microbial preparation, which is prepared by culturing a microorganism up to a desired density, and, if necessary, separating, washing, purifying and concentrating it, or a microbial preparation, which is prepared by further suspending the microorganism prepared above in an aqueous solution including, e.g., a buffer solution, can be used.

When the microbial preparation is used in a solid state, after a microorganism is cultured up to a desired density, if necessary, e.g., trehalose, sodium glutamate or skim milk is added as a lyophilization protectant thereto and then lyophilized. The lyophilized microbial cells can be directly used as a microbial preparation or a mixture of the lyophilized microbial cells and various additives can be used as a microbial preparation.

A microbial preparation of the present invention contains at least one selected from a microorganism belonging to the genus *Comamonas*, a microorganism belonging to the genus *Burkholderia*, a microorganism belonging to the genus *Paraburkholderia* and a microorganism belonging to the genus *Pseudomonas*, as an active ingredient. The microorganism has hydroxymethylfurfural and/or furfural oxidase activity.

Examples of the above microorganism are the same as described in Section 1 (3). Of them, the microorganism belonging to the genus *Comamonas* is preferably *Comamonas testosteroni* and *Comamonas thiooxydans*; the microorganism belonging to the genus *Burkholderia* is preferably *Burkholderia multivorans*; the microorganism belonging to the genus *Paraburkholderia* is preferably *Paraburkholderia xenovorans*; and the microorganism belonging to the genus *Pseudomonas* is preferably *Pseudomonas putida.*

A microbial preparation of the present invention contains the microorganism as mentioned above and a component(s) required for maintaining the microorganism and is used by adding it to activated sludge. Alternatively, a microorganism of the present invention is mixed with an existing activated sludge and used as a microbial preparation.

3. Microbial Preparation for Degrading Furan Compound

The present invention provides a microbial preparation for degrading a furan compound as mentioned above. A target furan compound, although it is not particularly limited, is preferably a furan-aldehyde such as furfural and tetrahydrofurfural.

The microbial preparation of the present invention for degrading a furan compound contains at least one of *Comamonas testosteroni, Comamonas thiooxydans* and *Paraburkholderia xenovorans* and a component(s) required for maintaining the microorganism and is used for degradation of a furan compound.

4. Use of Microorganism for Wastewater Treatment or Degradation of Furan Compound.

The present invention provides use of a microorganism as described in Section 1 (3) in treatment for wastewater containing a furan compound or degradation of a furan compound. The use of a microorganism can be carried out in accordance with the description of Section 1.

5. Method for Culturing Microorganism.

The present invention provides a method for culturing, at a high density, a microorganism belonging to the genus *Comamonas*, a microorganism belonging to the genus *Burkholderia* or a microorganism belonging to the genus *Paraburkholderia*.

As used herein, "culturing at a high density" or "high density culture" refers to culturing a microorganism at a high density. The "high concentration (high density)", although it is not particularly limited, means that an optical density ($OD_{660}$) of a medium containing a microorganism at a wavelength of 660 nm at a time point of 24 hours after initiation of culture is, for example, 15 or more, preferably 16 or more, more preferably 18 or more and further preferably 20 or more. Alternatively, "high concentration (high density)" means that an optical density ($OD_{660}$) of a medium containing a microorganism at a wavelength of 660 nm at a time point of 48 hours after initiation of culture is, for example, 20 or more, preferably 21 or more, more preferably 22 or more, further preferably 23 or more and particularly preferably 25 or more.

Density ($OD_{660}$) can be measured by diluting a culture solution and then using an ultraviolet-visible spectrophotometer (UV-1280 Shimadzu Corporation).

The culture method of the present invention increases a proliferation rate of the microorganism, thus allowing for the high density culture as mentioned above.

The proliferation rate of a microorganism can be measured by a common method such as a direct microscopic observation, a plate-culture method, a turbidimetric measurement and gravimetric measurement. In the gravimetric measurement, the proliferation rate can be calculated by dividing the dry weight of a microbial cell by culturing time. The dry weight of a microbial cell of a microorganism is determined by placing a predetermined volume of a culture solution previously cleaned in a weighing tube or on an aluminum dish previously weighed, drying the solution, weighing it again, obtaining a change (difference) in weight before and after drying and determining a dry weight/volume based on the change (difference).

According to the culture method of the present invention, the proliferation rate of a microorganism is 0.2 g/L/hr or more, preferably 0.3 g/L/hr or more and more preferably 0.4 g/L/hr or more on a basis of dry weight of a microbial cell (g-DCW/L) according to gravimetric measurement.

(1) Microorganism

A target microorganism of the culture method of the present invention is a microorganism belonging to the genus *Comamonas*, a microorganism belonging to the genus *Burkholderia*, or a microorganism belonging to the genus *Paraburkholderia*. Examples of these microorganisms are the same as described in Section 1 (3).

(2) Culture of Microorganism (Main Culture)

(2-1) Culture Medium

The culture medium is the one providing a growth environment for a microorganism to be cultured, and more specifically refers to the one prepared by dissolving, e.g., a carbon source, a nitrogen source and inorganic salts in an aqueous medium such as water.

The "primary medium" refers to a medium in which culture (main culture) is initiated by inoculating a preculture (seed), when culture is carried out in accordance with a feeding culture system (described later).

The "feed medium" refers to a medium, which is continuously or intermittently added to a primary medium during the culture time (process) after initiation of culture in the primary medium.

In the present invention, the primary medium and feed medium for culturing a microorganism belonging to the genus *Burkholderia* or a microorganism belonging to the genus *Paraburkholderia* contain gluconic acid. The primary medium and feed medium for culturing a microorganism belonging to the genus *Comamonas* contain at least one selected from gluconic acid, ethanol and succinic acid.

The primary medium and feed medium are preferably sterilized and put in use for culturing. A method for sterilizing a culture medium is not limited as long as the culture medium is in an aseptic condition where no proliferative microorganisms are present. Examples of the sterilization method include autoclaved sterilization (heat sterilization in autoclave at, for example, 121° C. for 20 minutes) and filter sterilization (filtration by a filter having, for example, a pore size of 0.45 m or 0.2 m). In the case of heat sterilization, if there is concern that reactions between components of a culture medium may occur, one type or more components of the culture medium may be sterilized separately from the other culture-medium components, and thereafter, combined.

(2-1-1) Primary Medium

The primary medium is satisfactory as long as it contains, e.g., a carbon source, a nitrogen source and inorganic salts which can be utilized by the microorganism of the invention and it is a medium in which the microorganism can be cultured at a high density in a short time.

Examples of the carbon source include carbohydrates such as glucose, galactose, fructose, sucrose, raffinose and starch; organic acids such as acetic acid, propionic acid, gluconic acid and succinic acid; and alcohols such as ethanol and propanol.

As mentioned above, the primary medium of the present invention contains at least one selected from gluconic acid, ethanol and succinic acid and preferably gluconic acid and/or ethanol.

Examples of the nitrogen source that can be used include complex-medium components derived from natural products (e.g., microorganism, plant, animal milk or animal meat); ammonium salts of inorganic acids or organic acids, such as ammonium chloride, ammonium sulfate, ammonium acetate and ammonium phosphate; ammonia; and others such as amino acids and nitrogen compounds.

Examples of the inorganic salts include monopotassium phosphate, dipotassium phosphate, magnesium phosphate, magnesium sulfate, sodium chloride, ferrous sulfate, manganese sulfate, zinc sulfate, copper sulfate, calcium carbonate and ammonium molybdenum heptamolybdate.

The primary medium may contain, if necessary, components other than the aforementioned components, such as vitamins and a defoaming agent for preventing foaming of a culture medium during culture.

As a basic medium for the primary medium, an inorganic medium commonly known in the technical field can be used. Examples of the inorganic medium includes K1 mineral medium (JOURNAL OF BACTERIOLOGY, December 2005, p. 7996-8005); *P. putida* medium (Biotechnology and Bioengineering, Vol. 112, No. 4, April, 2015); and MM medium (dipotassium hydrogen phosphate 3.9 g/L, ammonium sulfate 2.0 g/L, potassium dihydrogen phosphate dihydrate 2.1 g/L, EDTA 10.0 mg/L, magnesium chloride hexahydrate 100 mg/L, zinc sulfate heptahydrate 2.0 mg/L, iron sulfate heptahydrate 5.0 mg/L, manganese chloride tetrahydrate 10 mg/L, copper sulfate pentahydrate 0.2 mg/L, cobalt chloride hexahydrate 0.4 mg/L, ammonium molybdenum heptamolybdate tetrahydrate 0.2 mg/L, calcium chloride dihydrate 1.0 mg/L). Of them, MM medium is preferred.

In the present invention, when a microorganism belonging to the genus *Burkholderia* or a microorganism belonging to the genus *Paraburkholderia* is cultured, gluconic acid is added to an inorganic medium as mentioned above for use. When a microorganism belonging to the genus *Comamonas* is cultured, at least one selected from gluconic acid, ethanol and succinic acid, and preferably gluconic acid and/or ethanol is added to an inorganic medium as mentioned above for use.

As the gluconic acid, for example, a salt of gluconic acid such as sodium gluconate and potassium gluconate, may be used. As the succinic acid, a salt of succinic acid such as sodium succinate and potassium succinate, may be used.

The amount of gluconic acid to be used is not particularly limited as long as a microorganism can be cultured at a high concentration. The amount of gluconic acid can be, for example, 50 g/L or less, preferably 30 g/L or less, more preferably 10 g/L or less based on the total amount of a medium at the time of initiation of culture. If the amount is 10 g/L or less, the microorganism can be cultured at a higher concentration in a higher yield. In contrast, the amount is set at 110 g/L or less because it is difficult to obtain a higher effect even if the amount is further increased.

The amount of ethanol to be used is not particularly limited as long as a microorganism can be cultured at a high concentration. The amount of ethanol can be, for example, 30 g/L or less, preferably 20 g/L or less, and more preferably 10 g/L or less based on the total amount of a medium at the time of initiation of culture. If the amount is 10 g/L or less, the microorganism can be cultured at a higher concentration in a higher yield. In contrast, the amount is set at 110 g/L or less because it is difficult to obtain a higher effect, even if the amount is further increased.

The amount of succinic acid to be used is not particularly limited as long as a microorganism can be cultured at a high concentration. The amount of succinic acid can be, for example, 50 g/L or less, preferably 30 g/L or less, and more preferably 10 g/L or less based on the total amount of a medium at the time of initiation of culture. If the amount is 10 g/L or less, the microorganism can be cultured at a higher concentration in a higher yield. In contrast, the amount is set at 110 g/L or less because it is difficult to obtain a higher effect even if the amount is further increased.

(2-1-2) Feed Medium

In the present invention, in order to obtain a microorganism cultured at a high density, it is preferable to add feed medium to the primary medium during culture (culture process).

The components of the feed medium are not limited as long as a sufficient growth rate of a microorganism during culture can be maintained. In the present invention, the same components as in the primary medium can be used.

For culturing a microorganism belonging to the genus *Burkholderia* or a microorganism belonging to the genus *Paraburkholderia*, the feed medium contains gluconic acid. For culturing a microorganism belonging to the genus *Comamonas*, the feed medium contains at least one selected from gluconic acid, ethanol and succinic acid.

Other components and the amounts thereof are not limited as long as a sufficient growth rate of a microorganism can be maintained during culture and can be appropriately selected by those skilled in the art.

The volume of the feed medium to be added is not limited as long as a microorganism used in the present invention can sufficiently grow. The volume of the feed medium is, for example, 0.1 time or more and the same volume or less, preferably 0.15 times or more and 0.75 times or less, more preferably 0.2 times or more and 0.5 times or less as large as the volume of the primary medium. The volume is set to be 0.1 time or more because the microorganism can be cultured at a high density. In contrast, the amount is set to be 300 g/L or less because it is difficult to obtain a high effect comparable to the amount to be added even if the addition amount to the medium is further increased.

(2-2) Culture Method (2-2-1) Culture System

Examples of the culture method that can be used in the present invention include batch culture, feeding culture (semi-batch culture, fed batch culture), and continuous culture (perfusion culture). Of them, feeding culture is preferred.

The feeding culture system refers to a culture method in which culture is carried out by continuously or intermittently feeding (adding) a culture medium to a medium (for example, primary medium) during culture without removing the culture medium from the container until the end of culture.

A feeding mode is not limited as long as a genetically modified microorganism can be cultured at a high density in a short time to efficiently produce a recombinant protein. Examples of the feeding mode include constant-feeding mode, exponential feeding mode, stepwise increase feeding mode, specific growth-rate control feeding mode, pH stat feeding mode, DO-stat feeding mode, glucose concentration control feeding mode, acetic acid concentration monitoring feeding mode and pulse feeding mode.

The method for adding a feeding medium is not limited as long as growth/proliferation of a microorganism can be maintained during culture. For example, constant-feeding mode is a method in which a feed medium is continuously or intermittently fed at a constant flow rate on a basis of mass or volume. Note that, the flow rate is an amount of a fluid per unit time.

The pulse feed mode refers to a mode in which a feed medium is fed at a constant flow rate on a basis of mass or volume at points when dissolved oxygen begins to rise again after dissolved oxygen is consumed with degradation of a substrate.

A feed medium may be added at the time point when the dissolved oxygen in the primary medium is consumed up to 80 to 99.9%, preferably 85 to 99.5%, and more preferably at the time point when dissolved oxygen begins to rise again after it is consumed up to 90 to 99%. The pulse feed mode is preferably used in view of workload and improvement of the yield of microbial cells. This is because a microorganism can be cultured at a high density in a short time by adding a feed medium.

The amount and rate of the feed medium to be added are not limited as long as the concentrations of gluconic acid, ethanol and succinic acid in a culture medium are maintained during culture and the growth/proliferation of a microorganism is sufficiently maintained. For example, it is preferable to increase the concentrations of components in a culture medium, because the amount of the feed medium to be added is saved.

(2-2-2) Culture Temperature

The culture temperature is not limited as long as the microorganism to be used in the present invention sufficiently grows and proliferates. The temperature can be set at, for example, 10° C. to 45° C., preferably 15° C. to 40° C., and more preferably 20° C. to 37° C. The temperature can be changed, if necessary, during culture. If the culture temperature is set at 10° C. or more, a microorganism can be cultured at a high concentration. If the culture temperature is set at 45° C., a decrease of the culture rate can be suppressed.

(2-2-3) pH

The pH of a culture medium during culture is not limited as long as the microorganism to be used in the present invention sufficiently grows and proliferates. The pH of a culture medium can be set at, for example, 3 to 9, preferably 3.5 to 8.5 and more preferably 5 to 8. A microorganism can be cultured at a high density in a short time if it is cultured within the range of pH.

For controlling the pH of the culture medium during culture, inorganic or organic acid or alkali solution can be used. As the acid, an inorganic acid is preferably used. Examples of the acid include sulfuric acid, phosphoric acid, hydrochloric acid and nitric acid. Examples of the alkali include potassium hydroxide, sodium hydroxide and ammonia.

(2-2-4) Aeration

A culture solution can be aerated during culture. For example, when the microorganism to be used in the present invention is densely cultured at a high concentration, the culture medium is preferably aerated with a gas containing a higher concentration of oxygen. The concentration of oxygen to be contained in the aeration gas can be appropriately selected depending on, e.g., the type of microorganism to be cultured and culture conditions. The oxygen concentration can be set at, for example, 20% (v/v) or more, preferably 50% (v/v) or more, and more preferably 90% (v/v) or more. If a culture medium is aerated with a gas containing 90% (v/v) or more of oxygen, proliferation of a microorganism is promoted.

The air-flow rate can be appropriately selected depending on the culture conditions including the size of a culture tank and the type of microorganism to be cultured. The air-flow rate can be, for example, 0.6 to 10 vvm (1.2 to 20 L/min), preferably 0.8 to 8 vvm (1.6 to 16 L/min) and more preferably 1 to 5 vvm (2 to 10 L/min). If the air-flow rate is set at 0.6 vvm or more, a microorganism can be cultured at a high concentration. The air-flow rate is defined to be 10 vvm or less because it is difficult to obtain a higher effect than above even if the air-flow rate is further increased.

(2-2-5) Pressure

The pressure during culture is not particularly limited. Culture can be made under atmospheric pressure and, if necessary, under increased pressure. As the pressure, culture can be carried out under increased pressure of, for example, 0 to 0.5 MPa, preferably 0.01 to 0.3 MPa and more preferably 0.02 to 0.2 MPa. Since the concentration of dissolved oxygen in a culture medium is increased by pressurization, a microorganism can be cultured at a higher concentration.

(2-2-6) Stirring

In the present invention, culture can be made while stirring a culture solution at need. The stirring rate can be appropriately selected depending on the culture conditions and the type of microorganism. The stirring rate can be set at, for example, 10 to 2500 rpm, preferably 20 to 2000 rpm, and more preferably 30 to 1500 rpm. If the stirring rate is set at 10 rpm or more, a microorganism can be cultured at a high concentration. If the stirring rate is set at 3000 rpm or less, stress to a microorganism can be reduced.

(2-2-7) Culture Time

The culture time is not limited as long as a microorganism grows and proliferates at a sufficiently high concentration. The culture time may be set at, for example, about 5 to 120 hours, preferably 10 to 100 hours, further preferably 15 to 80 hours, and still further preferably 20 to 60 hours. The ending time of culture is not particularly limited and culture may be terminated after a microorganism is obtained at a desired density (amount).

(2-2-8) Other Conditions

In the present invention, pre-culture can be carried out as needed. Pre-culture is a culture process for preparing a seed which is to be inoculated in a culture (main culture) for culturing a microorganism at a high density. If the pre-culture is appropriately carried out, the amount of microbial cells required as a seed for a main culture can be obtained.

The culture medium for use in pre-culture is not particularly limited as long as it does not inhibit high density culture of a microorganism in a main culture. The medium for pre-culture can contain, for example, the same carbon source, nitrogen source and inorganic salts, as in the primary culture medium of a main culture and, if necessary, may contain the other components. The culture temperature, pH, pressure and culture time during pre-culture are not limited as long as they do not inhibit growth of a microorganism in a main culture.

The culture temperature may be, for example, 10° C. to 45° C., preferably 15° C. to 45° C. and more preferably 20° C. to 37° C. The pH of a culture medium during culture may be controlled with an acid and an alkali to fall within a predetermined range similarly to a main culture but the pH control is not essential. For example, the pH of the culture medium is controlled to be 3 to 9, preferably 3.5 to 8.5 and more preferably 5 to 8 when a culture medium is prepared. During culture, pH may not be controlled. As the pressure, culture may be carried out in atmospheric pressure and, if necessary, can be carried out under pressure of 0 to 0.1 MPa and preferably 0.01 to 0.05 MPa. The culture time is not particularly limited as long as it is sufficient to obtain the amount of microbial cells required for culturing a microorganism at a high density in a main culture. The culture time may be set at, for example, 0.5 to 48 hours, preferably 1 to 30 hours and more preferably 3 to 24 hours.

Since the culture solution obtained by the culture method of the present invention contains a microorganism at a high concentration, the culture solution can be directly used as a microbial preparation.

A microorganism may be washed, further concentrated, or used with the addition of additives such as a preservative and a stabilizer, if necessary.

A microorganism can be lyophilized, if necessary, with the addition of a lyophilization protectant such as trehalose, sodium glutamate and skim milk. The lyophilized microbial cells can be directly used as a microbial preparation or a mixture of the lyophilized microbial cells and various additives can be used as a microbial preparation.

Since the microorganism to be used in the present invention can degrade, e.g., furfural, acetic acid and formic acid, a microbial preparation as mentioned above can be used for treatment for wastewater described in Section 1.

EXAMPLES

The present invention will be more specifically described by way of Examples; however, the present invention is not limited to these Examples.

[PART I]

[Test Example 1] Time-Dependent Degradation Test for Furan Compound Contained in Wastewater with *Comamonas testosteroni* NBRC12047 Strain To 20 mL of a liquid medium containing furfural, formic acid and acetic acid whose concentrations were adjusted to be 100 ppm, 1000 ppm and 1300 ppm, respectively, and placed in a 200 mL-conical flask, *Comamonas testosteroni* NBRC12047 strain was added so as to obtain a final $OD_{660}$=0.005. The flask was closed with a cotton stopper and shaken at 30° C. and 230 rpm. A sample was taken at time points of 0, 7, 24 and 48 hours. A suspended matter in the samples was filtered by a 0.45 μm filter and the concentrations of furfural, formic acid and acetic acid of the samples were measured by HPLC.

Measurement conditions were as follows. Furfural was measured by use of a Nakalai 5C18-MS-II (4.6 ID×250 mm) column for 20 minutes by setting the ratio of 20 mM formic acid and methanol at 20:80. Formic acid, acetic acid and xylose were measured by an ULTRON PS-80H (ID 8.0 mm×300 mm) column with 0.108% perchloric acid for 20 minutes.

The results are shown in FIG. 1. As is apparent from FIG. 1, it was confirmed that furfural present in a concentration of 100 ppm was degraded and decreased up to 0 pm; formic acid (1000 ppm) decreased up to 130 ppm; and acetic acid (1300 ppm) decreased up to 0 ppm, in 48 hours.

Figure 2:
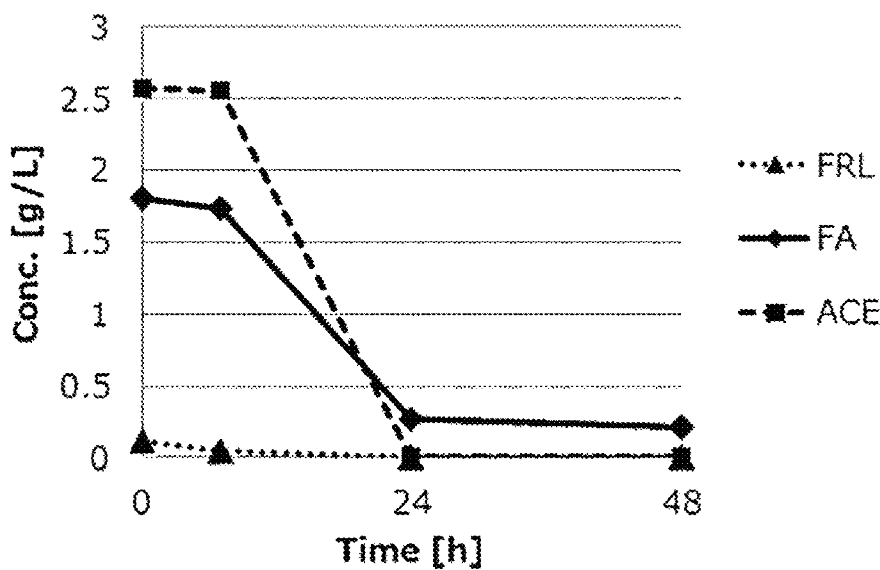
FIG. 2 The figure shows degradation of furfural, formic acid and acetic acid by *Comamonas thiooxydans* NBRC 110656 strain (change in concentration for over 48 hours). The vertical axis represents concentration [g/L] and the horizontal axis represents time [h] (dotted line: ▲ (FRL: furfural), solid line: ♦ (FA: formic acid), dashed line: ■ (ACE: acetic acid)).

[Test Example 2] Time-Dependent Degradation Test for Furan Compound Contained in Wastewater with *Comamonas Thiooxydans* NBRC 110656 Strain The same procedure as in Test Example 1 was repeated except that *Comamonas thiooxydans* NBRC 110656 strain was added so as to obtain a final $OD_{660}$=0.005 in a liquid medium containing furfural, formic acid and acetic acid whose concentrations were adjusted to be 100 ppm, 1800 ppm and 2500 ppm, respectively. The results are shown in FIG. 2. As is apparent from FIG. 2, it was confirmed that furfural present in a concentration of 100 ppm was degraded and decreased up to 0 pm, formic acid (1800 ppm) decreased up to 220 ppm and acetic acid (2500 ppm) decreased up to 0 ppm, in 48 hours.

Figure 3:
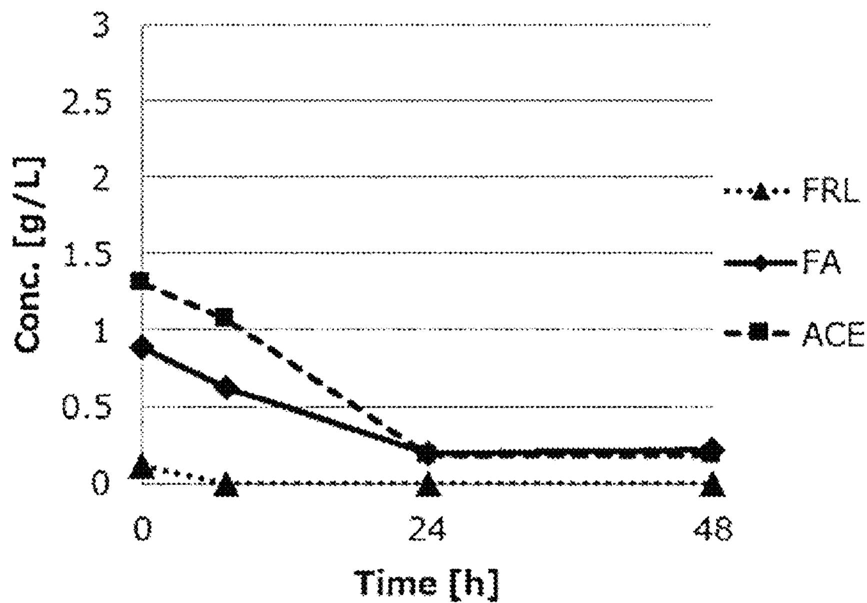
FIG. 3 The figure shows degradation of furfural, formic acid and acetic acid by *Paraburkholderia xenovorans* DSM17367 strain (change in concentration for over 48 hours). The vertical axis represents concentration [g/L] and the horizontal axis represents time [h] (dotted line: ▲ (FRL: furfural), solid line: ♦ (FA: formic acid), dashed line: ■ (ACE: acetic acid)).
Figure 4:
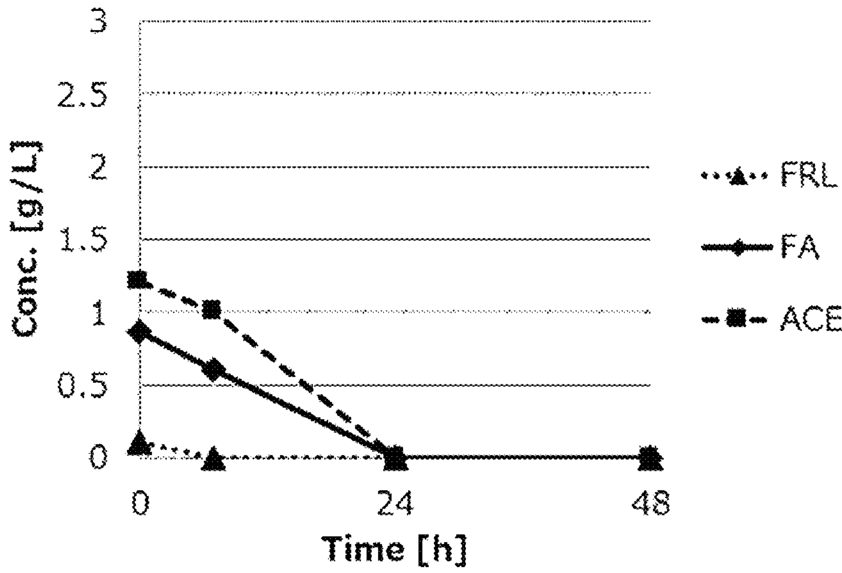
FIG. 4 The figure shows degradation of furfural, formic acid and acetic acid by *Pseudomonas putida* NBRC3738 strain (change in concentration for over 48 hours). The vertical axis represents concentration [g/L] and the horizontal axis represents time [h] (dotted line: ▲ (FRL: furfural), solid line: ♦ (FA: formic acid), dashed line: ■ (ACE: acetic acid)).

[Test Example 3] Time-Dependent Degradation Test for Furan Compound Contained in Wastewater with *Paraburkholderia xenovorans* DSM17367 Strain The same procedure as in Test Example 1 was repeated except that *Paraburkholderia xenovorans* DSM17367 strain was added so as to obtain a final $OD_{660}$=0.005 in a liquid medium containing furfural, formic acid and acetic acid whose concentrations were adjusted to be 100 ppm, 900 ppm and 1300 ppm, respectively. The results are shown in FIG. 3. As is apparent from FIG. 3, it was confirmed that furfural present in a concentration of 100 ppm was degraded and decreased up to 0 pm, formic acid (900 ppm) decreased up to 200 ppm and acetic acid (1300 ppm) decreased up to 180 ppm, in 48 hours.

Figure 5:
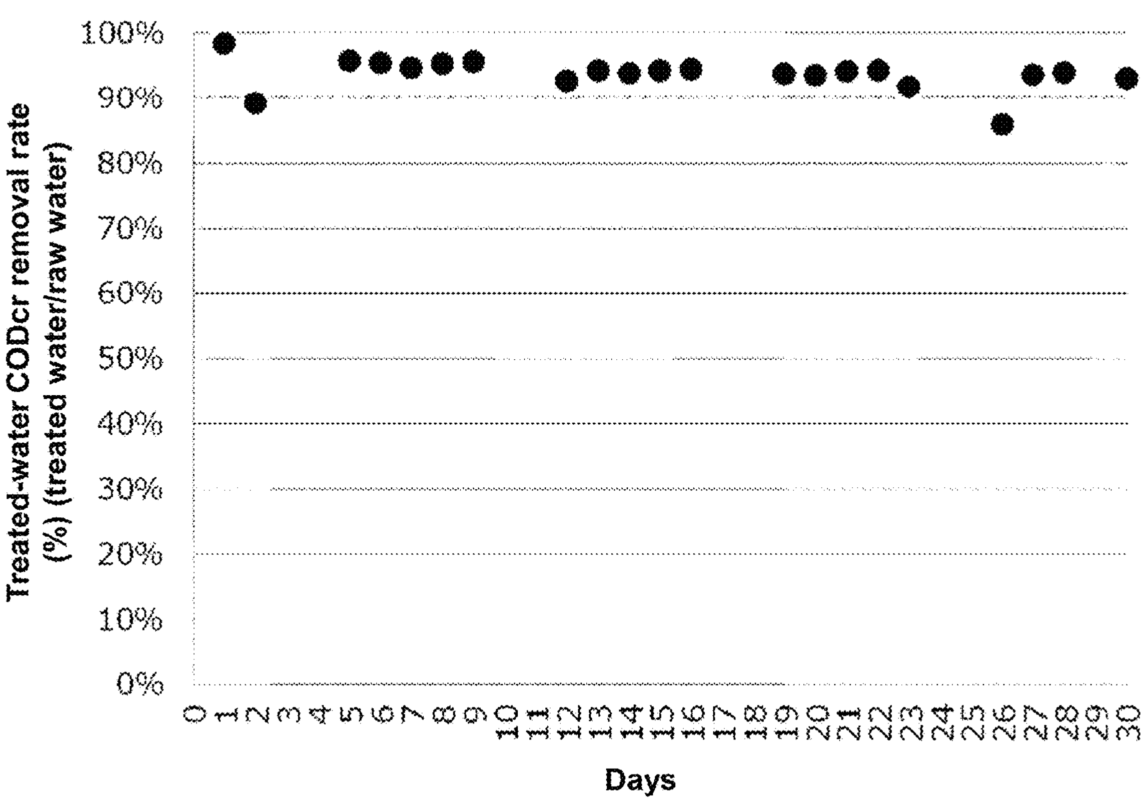
FIG. 5 The figure shows a time-dependent change of CODcr removal rate of treated water by *Comamonas testosteroni* NBRC12047 strain when a membrane separator was used. The vertical axis represents CODcr removal rate % (treated water/raw water) and the horizontal axis represents days.

[Test Example 4] Time-Dependent Degradation Test for Furan Compound Contained in Wastewater with *Pseudomonas putida* NBRC3738 Strain The same procedure as in Test Example 1 was repeated except that *Pseudomonas putida* NBRC3738 strain was added so as to obtain a final $OD_{660}$=0.005 in a liquid medium containing furfural, formic acid and acetic acid whose concentrations were adjusted to be 100 ppm, 900 ppm and 1200 ppm, respectively. The results are shown in FIG. 5. As is apparent from FIG. 5, it was confirmed that furfural present in a concentration of 100 ppm was degraded and decreased up to 0 pm, formic acid (900 ppm) decreased up to 0 ppm and acetic acid (1200 ppm) decreased up to 0 ppm, in 48 hours.

[Test Example 5] Time-Dependent Degradation Test for Furan Compound Contained in Wastewater with *Burkholderia multivorans* NBRC 102086 Strain The same procedure as in Test Example 1 was repeated except that *Burkholderia multivorans* NBRC 102086 was added so as to obtain a final $OD_{660}$=0.005 in a liquid medium containing furfural, formic acid and acetic acid whose concentrations were adjusted to be 100 ppm, 1800 ppm and 2500 ppm, respectively.

[Test Example 6] Time-Dependent Treatment Test for Furan Compound Contained in Wastewater with *Comamonas testosteroni* NBRC12047 Strain in Membrane Separator Twenty hollow-fiber microfiltration membranes ("SADF membrane" made of polyvinylidene fluoride and manufactured by Mitsubishi Chemical Corporation) were arranged at regular intervals within the range of 105 mm in width, and then, both ends of the hollow-fiber microfiltration membranes were connected to an annular support. In this manner, an unclosed (open) membrane module (effective membrane length 125 mm, membrane area 0.022 $m^2$) was prepared. The membrane module was disposed above a diffuser tube in an aeration tank (width 10 cm, depth 12 cm, height 35 cm) such that the length direction (long side) of the membrane is parallel to the vertical direction to prepare a Membrane Bio Reactor.

The Membrane Bio Reactor was charged with 2000 mL of activated sludge (pH 7.0) collected from a wastewater treatment facility in the property of the Science & Innovation Center of Mitsubishi Chemical Corporation so as to contain an MLSS of 4000 mg/L. Membrane filtration was initiated at a treatment temperature of 30° C. and an aeration volume of 10 L/min, by supplying wastewater at a flow rate of 720 mL/day to obtain treated water. The wastewater contained furfural, formic acid, acetic acid and xylose whose concentrations were adjusted to be 100 ppm, 2000 ppm, 200 ppm and 550 ppm, respectively, and *Comamonas testosteroni* NBRC12047 strain was added so as to obtain a final $OD_{660}$=0.005. A sample was taken from the water filtered by the membrane, every day. TOC (total organic carbon) in the samples was measured by TOC analyzer (TOC-V SCN, Shimadzu Corporation) in accordance with combustion oxidation-infrared type TOC analysis method according to "JIS K-0102 testing methods for industrial wastewater". CODcr values in samples were determined (obtained) by multiplying TOC values of individual samples with the correlation coefficient, which was obtained from samples whose TOC values and CODcr values were known. The results are shown in FIG. 5. As is apparent from FIG. 5, it was confirmed that CODcr removal rate of the treated water is maintained at a level of about 90% or more for 27 days.

[Test Example 7] Activated Carbon Treatment Test of Wastewater Obtained after Treatment of Wastewater Containing a Furan Compound with *Comamonas testosteroni* NBRCl2047 Strain and Activated Sludge The wastewater obtained in Test Example 6 was supplied to a column charged with activated carbon (manufactured by Mitsubishi Chemical Aqua Solutions Co., Ltd.) up to a height of 35 cm, and allowed to fall by gravity and pass through the wastewater so as to obtain a linear velocity of 1.3 m/h and a space velocity of 41/h, for 2 hours. The CODcr value of 620 ppm of the wastewater before passing through the column decreased to 30 ppm after the wastewater passed through the column.

[Test Example 8] Fenton's Catalyst Treatment Test of Wastewater Obtained after Treatment of Wastewater Containing a Furan Compound with *Comamonas testosteroni* NBRC12047 Strain and Activated Sludge The wastewater obtained in Test Example 6 was added in a 50-mL Falcon tube and iron sulfate heptahydrate and hydrogen peroxide were added thereto each in a molar quantity twice as large as that of TOC in the wastewater, and thereafter, allowed to stand still at normal temperature (25°

C.) for one hour. After formation of a precipitate, the supernatant of a sample was filtered by a 0.45 μm filter. The CODcr value of 520 ppm before treatment decreased to 102 ppm after the Fenton's catalyst treatment.

[Test Example 9] Peroxidase or Laccase Treatment Test of Wastewater Obtained after Treatment of Wastewater Containing a Furan Compound with *Comamonas testosteroni* NBRC12047 Strain and Activated Sludge The wastewater obtained in Test Example 6 was added in a 50-mL Falcon tube, hydrogen peroxide, peroxidase (derived from Brassicaceae horseradish (*Armorica rusticana*) and manufactured by FUJIFILM Wako Pure Chemical Corporation) and laccase (derived from *Trametes versicolor*, Sigma-Aldrich) were added so as to be 10 ppm, 5 ppm and 5 ppm, respectively, and then, allowed to stand alone at normal temperature for 24 hours. After formation of a precipitate, the supernatant of a sample was filtered by a 0.45 μm filter. The CODcr value of 620 ppm before treatment decreased to 110 ppm after the treatment with hydrogen peroxide and peroxidase and decreased to 100 ppm after the treatment with laccase.

Figure 6:
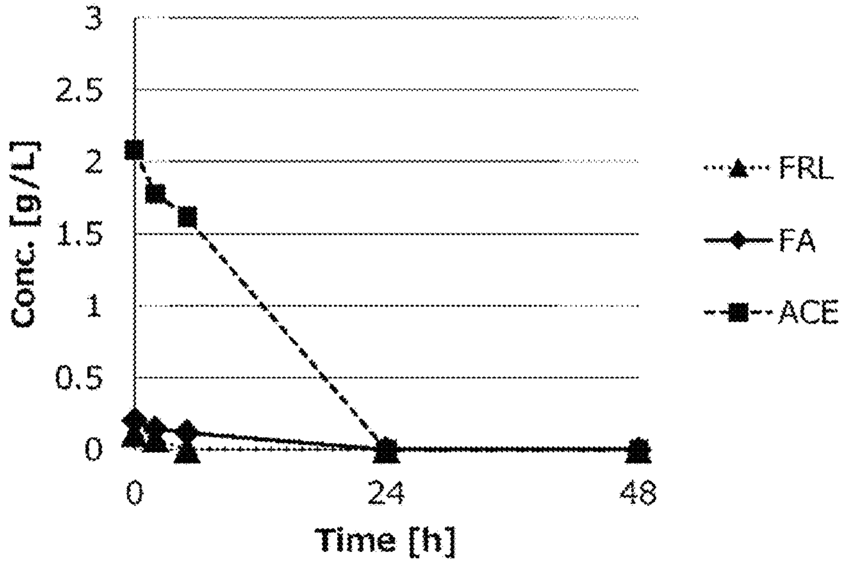
FIG. 6 The figure shows degradation of furfural, formic acid and acetic acid by *Burkholderia multivorans* NBRC102086 strain (change in concentration for over 48 hours). The vertical axis represents concentration [g/L] and the horizontal axis represents time [h] (dotted line: ▲ (FRL: furfural), solid line: ♦ (FA: formic acid), dashed line: ■ (ACE: acetic acid)).

[Test Example 10] Time-Dependent Degradation Test for Furan Compound Contained in Wastewater with *Burkholderia multivorans* NBRC102086 Strain The same procedure as in Test Example 1 was repeated except that *Burkholderia multivorans* NBRC 102086 strain was added so as to be a final $OD_{660}$=0.1 in a liquid medium containing furfural, formic acid and acetic acid whose concentrations were adjusted to be 100 ppm, 200 ppm and 2000 ppm, respectively. The results are shown in FIG. 6. As is apparent from FIG. 6, it was confirmed that furfural present in a concentration of 100 ppm was degraded and decreased up to 0 ppm, formic acid (200 ppm) decreased up to 0 ppm and acetic acid (2000 ppm) decreased up to 0 ppm, in 48 hours.

Figure 7:
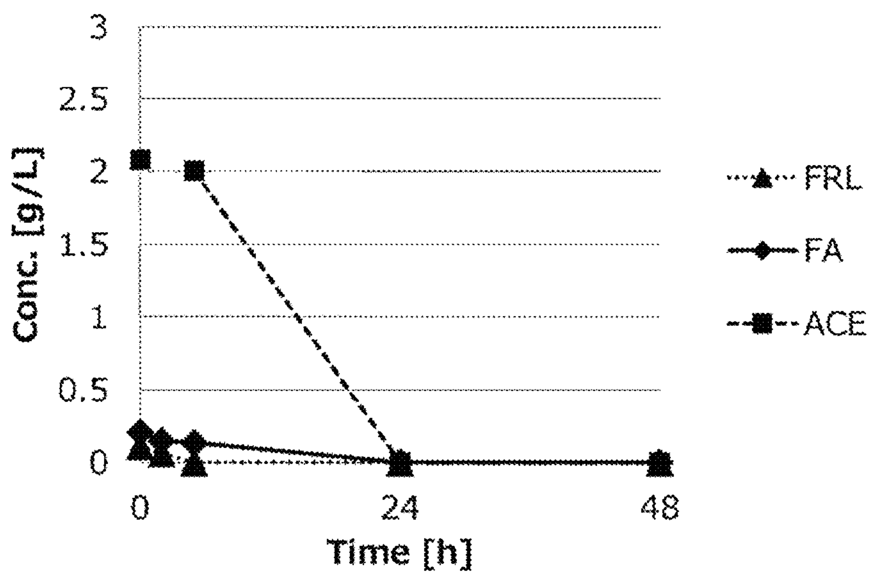
FIG. 7 The figure shows degradation of furfural, formic acid and acetic acid by *Paraburkholderia caledonica* NBRC102488 strain (change in concentration for over 48 hours). The vertical axis represents concentration [g/L] and the horizontal axis represents time [h] (dotted line: ▲ (FRL: furfural), solid line: ♦ (FA: formic acid), dashed line: ■ (ACE: acetic acid)).

[Test Example 11] Time-Dependent Degradation Test for Furan Compound Contained in Wastewater with *Paraburkholderia caledonica* NBRC102488 Strain The same procedure as in Test Example 1 was repeated except that *Paraburkholderia caledonica* NBRC102488 strain was added so as to be a final $OD_{660}$=0.1 in a liquid medium containing furfural, formic acid and acetic acid whose concentrations were adjusted to be 100 ppm, 200 ppm and 2000 ppm, respectively. The results are shown in FIG. 7. As is apparent from FIG. 7, it was confirmed that furfural present in a concentration of 100 ppm was degraded and decreased up to 0 ppm, formic acid (200 ppm) decreased up to 0 ppm and acetic acid (2000 ppm) decreased up to 0 ppm, in 48 hours.

Figure 8:
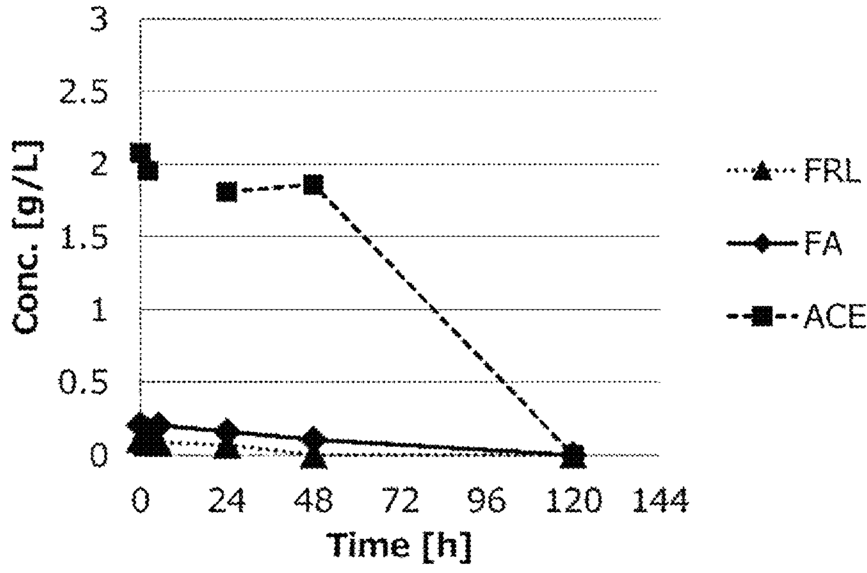
FIG. 8 The figure shows degradation of furfural, formic acid and acetic acid by *Pseudomonas oryzihabitans* NBRC102199 strain (change in concentration for over 48 hours). The vertical axis represents concentration [g/L] and the horizontal axis represents time [h] (dotted line: ▲ (FRL: furfural), solid line: ♦ (FA: formic acid), dashed line: ■ (ACE: acetic acid)).

[Test Example 12] Time-Dependent Degradation Test for Furan Compound Contained in Wastewater with *Pseudomonas oryzihabitans* NBRC102199 Strain The same procedure as in Test Example 1 was repeated except that *Pseudomonas oryzihabitans* NBRC102199 strain was added so as to be a final $OD_{660}$=0.1 in a liquid medium containing furfural, formic acid and acetic acid whose concentrations were adjusted to be 100 ppm, 200 ppm and 2000 ppm, respectively. The results are shown in FIG. 8. As is apparent from FIG. 8, it was confirmed that furfural present in a concentration of 100 ppm was degraded and decreased up to 0 ppm, formic acid (200 ppm) decreased up to 0 ppm and acetic acid (2000 ppm) decreased up to 0 ppm, in 120 hours.

[PART II]

1. Search for Optimal Carbon Source by Test Tube Culture

Example 1

(Main Culture)

Colonies of *Comamonas testosteroni* NBRC 12047 strain were inoculated to 3 mL of a main culture medium prepared in 15 mL test tubes and cultured while shaking at temperature of 30° C. and a rotation number of 200 rpm for 16 hours.

The main culture medium was prepared by dissolving components (sodium gluconate 10 g/L, dipotassium hydrogen phosphate 3.9 g/L ammonium sulfate 2.0 g/L, potassium dihydrogen phosphate dihydrate 2.1 g/L, EDTA 10.0 mg/L, magnesium chloride hexahydrate 100 mg/L, zinc sulfate heptahydrate 2.0 mg/L, iron sulfate heptahydrate 5.0 mg/L, manganese chloride tetrahydrate 10 mg/L, copper sulfate pentahydrate 0.2 mg/L, cobalt chloride hexahydrate 0.4 mg/L, ammonium molybdenum heptamolybdate tetrahydrate 0.2 mg/L, calcium chloride dihydrate 1.0 mg/L) in water, diluting the solution in a measuring flask and thereafter sterilizing it with heat (121° C., 20 minutes).

Measurement of the microbial density was determined by measuring absorbance ($OD_{660}$) at 660 nm. The results are shown in Table 1.

Example 2

Culture was carried out in the same manner as in Example 1 except that disodium succinate (10 g/L) was used in place of sodium gluconate in the main culture medium. The results are shown in Table 1.

Example 3

Culture was carried out in the same manner as in Example 1 except that glycerol (10 g/L) was used in place of sodium gluconate in the main culture medium. The results are shown in Table 1.

Example 4

Culture was carried out in the same manner as in Example 1 except that ethanol (10 g/L) was used in place of sodium gluconate in the main culture medium. The results are shown in Table 1.

Comparative Example 1

Culture was carried out in the same manner as in Example 1 except that glucose (10 g/L) was used in place of sodium gluconate in the main culture medium. The results are shown in Table 1.

Comparative Example 2

Culture was carried out in the same manner as in Example 1 except that xylose (10 g/L) was used in place of sodium gluconate in the main culture medium. The results are shown in Table 1.

Comparative Example 3

Culture was carried out in the same manner as in Example 1 except that sucrose (10 g/L) was used in place of sodium gluconate in the main culture medium. The results are shown in Table 1.

TABLE 1

| *Commamonas testosteroni* NBRC12047 | Carbon source | OD660 |
|---|---|---|
| Example 1 | Sodium gluconate | 0.21 |
| Example 2 | Disodium succinate | 2.00 |
| Example 3 | Glycerol | 0.03 |
| Example 4 | Ethanol | 0.01 |
| Comparative Example 1 | Glucose | 0.00 |
| Comparative Example 2 | Xylose | 0.00 |
| Comparative Example 3 | Sucrose | 0.00 |

From Table 1, it was confirmed that *Comamonas testosteroni* NBRC 12047 strain had a high microbial density at the time of 16 hours when sodium gluconate, disodium succinate, ethanol or glycerol was used as a carbon source, whereas the strain does not grow when glucose, xylose or sucrose was used as a carbon source.

Example 5

Culture was carried out in the same manner as in Example 1 except that *Burkholderia multivorans* NBRC 102086 strain was used as a microorganism. The results are shown in Table 2.

Example 6

Culture was carried out in the same manner as in Example 5 except that disodium succinate (10 g/L) was used in place of sodium gluconate in the main culture medium. The results are shown in Table 2.

Example 7

Culture was carried out in the same manner as in Example 5 except that glycerol (10 g/L) was used in place of sodium gluconate in the main culture medium. The results are shown in Table 2.

Example 8

Culture was carried out in the same manner as in Example 5 except that ethanol (10 g/L) was used in place of sodium gluconate in the main culture medium. The results are shown in Table 2.

Comparative Example 4

Culture was carried out in the same manner as in Example 5 except that glucose (10 g/L) was used in place of sodium gluconate in the main culture medium. The results are shown in Table 2.

Comparative Example 5

Culture was carried out in the same manner as in Example 5 except that xylose (10 g/L) was used in place of sodium gluconate in the main culture medium. The results are shown in Table 2.

Comparative Example 6

Culture was carried out in the same manner as in Example 5 except that sucrose (10 g/L) was used in place of sodium gluconate in the main culture medium. The results are shown in Table 2.

TABLE 2

| *Burkholderia multivorans* NBRC102086 | Carbon source | OD660 |
|---|---|---|
| Example 5 | Sodium gluconate | 1.34 |
| Example 6 | Disodium succinate | 1.11 |
| Example 7 | Glycerol | 0.00 |
| Example 8 | Ethanol | 0.00 |
| Comparative Example 4 | Glucose | 1.36 |
| Comparative Example 5 | Xylose | 0.43 |
| Comparative Example 6 | Sucrose | 0.02 |

Example 9

Culture was carried out in the same manner as in Example 1 except that *Paraburkholderia caledonica* NBRC102488 strain was used as a microorganism. The results are shown in Table 3.

Example 10

Culture was carried out in the same manner as in Example 9 except that disodium succinate (10 g/L) was used in place of sodium gluconate in the main culture medium. The results are shown in Table 3.

Example 11

Culture was carried out in the same manner as in Example 9 except that glycerol (10 g/L) was used in place of sodium gluconate in the main culture medium. The results are shown in Table 3.

Example 12

Culture was carried out in the same manner as in Example 9 except that ethanol (10 g/L) was used in place of sodium gluconate in the main culture medium. The results are shown in Table 3.

Comparative Example 7

Culture was carried out in the same manner as in Example 9 except that glucose (10 g/L) was used in place of sodium gluconate in the main culture medium. The results are shown in Table 3.

Comparative Example 8

Culture was carried out in the same manner as in Example 9 except that xylose (10 g/L) was used in place of sodium gluconate in the main culture medium. The results are shown in Table 3.

Comparative Example 9

Culture was carried out in the same manner as in Example 9 except that sucrose (10 g/L) was used in place of sodium gluconate in the main culture medium. The results are shown in Table 3.

TABLE 3

| *Paraburkholderia caledonica* NBRC102488 | Carbon source | OD660 |
|---|---|---|
| Example 9 | Sodium gluconate | 1.01 |
| Example 10 | Disodium succinate | 1.22 |
| Example 11 | Glycerol | 0.06 |
| Example 12 | Ethanol | 0.04 |
| Comparative Example 7 | Glucose | 1.28 |
| Comparative Example 8 | Xylose | 0.77 |
| Comparative Example 9 | Sucrose | 0.05 |

2. Optimization of Initial Sodium-Gluconate Concentration in Main Culture Medium by 1-L Jar Culture Example 13

(Pre-Pre Culture)

Colonies of *Comamonas testosteroni* NBRC 12047 strain were inoculated in a 3-mL pre-pre culture medium (LB Broth Miller Novagen catalog number: 71753-5CN) prepared in eight 15-mL test tubes and cultured with shaking at a temperature of 30° C., at a rotation number of 230 rpm for 8 hours.

The pre-pre culture medium was prepared by dissolving LB Broth Miller Novagen (25 g) in water, diluting the mixture up to 1000 mL in a measuring flask, and sterilizing it with heat (121° C., 20 minutes)

(Pre-Culture)

The pre-pre-culture solution (3 mL) obtained was inoculated (added) in a 100-mL pre-culture medium (LB Broth Miller Novagen catalog number: 71753-5CN) prepared in 500 mL-flasks and cultured with shaking at a temperature 30° C. and a rotation number of 230 rpm for 16 hours.

The pre-pre-culture medium was prepared by dissolving LB Broth Miller Novagen (2.5 g) in water, diluting the mixture up to 100 mL in a measuring flask and sterilizing it with heat (121° C., 20 minutes)

(Main Culture)

The pre-culture solution (200 mL) obtained was concentrated by a centrifuge. Concentrated microbial cells were inoculated in a 500-mL main-culture primary medium (sodium gluconate 10 g/L, dipotassium hydrogen phosphate 3.9 g/L ammonium sulfate 2.0 g/L, potassium dihydrogen phosphate dihydrate 2.1 g/L, EDTA 10.0 mg/L, magnesium chloride hexahydrate 100 mg/L, zinc sulfate heptahydrate 2.0 mg/L, iron sulfate heptahydrate 5.0 mg/L, manganese chloride tetrahydrate 10 mg/L, copper sulfate pentahydrate 0.2 mg/L, cobalt chloride hexahydrate 0.4 mg/L, ammonium molybdenum heptamolybdate tetrahydrate 0.2 mg/L, calcium chloride dihydrate 1.0 mg/L, LG-294 (1 g/L ADEKA CORPORATION)) prepared in a 1-L jar fermenter so as to obtain an initial $OD_{660}$ of 1.0, and cultured at a temperature 30° C. and a rotation number of 500 rpm, while aerating the medium with a gas containing 20% (v/v) of oxygen at a rate of 1.0 vvm, and controlling the lower limit of pH to be 6.95 and the upper limit of pH to be 7.05 (by use of a 1 N potassium hydroxide solution).

The main-culture primary medium was prepared by mixing a solution, which is prepared by dissolving required amounts of sodium gluconate, dipotassium hydrogen phosphate, ammonium sulfate and potassium dihydrogen phosphate dihydrate in water, diluting the solution up to 2000 mL in a measuring flask, and sterilizing it with heat (121° C., 20 minutes), and a solution of the other components (except sodium gluconate, dipotassium hydrogen phosphate, ammonium sulfate, potassium dihydrogen phosphate dihydrate), which was previously sterilized by a 0.20 μm-filter, in aseptic conditions.

The pH of the culture (medium) was maintained at about 7.0 until the end of culture. The culture solution obtained after 47-hour culture, was measured for microbial density by measuring absorbance ($OD_{660}$) at 660 nm. The results are shown in Table 4.

Comparative Example 10

Culture was carried out in the same manner as in Example 13 except that the amount of sodium gluconate was changed to 20 g/L in the main culture medium. The results are shown in Table 4.

Comparative Example 11

Culture was carried out in the same manner as in Example 13 except that inoculation was carried out so as to obtain an initial $OD_{660}$ of 0.5 and the main culture solution was collected after 23-hour culture. The results are shown in Table 4.

Comparative Example 12

Culture was carried out in the same manner as in Example 13 except that the amount of sodium gluconate was changed to 50 g/L in the main culture medium. The results are shown in Table 4.

Comparative Example 13

Culture was carried out in the same manner as in Example 13 except that the amount of sodium gluconate was changed to 100 g/L in the main culture medium. The results are shown in Table 3.

TABLE 4

| | Inoculation of microbial cells initial OD660 | Sodium gluconate initial concentration (g/L) | Culture time (hr) | OD660 |
|---|---|---|---|---|
| Example 13 | 1.00 | 10 | 47 | 14.0 |
| Comparative Example 10 | 1.00 | 20 | 47 | 10.0 |
| Comparative Example 11 | 0.50 | 20 | 23 | 4.9 |
| Comparative Example 12 | 0.50 | 50 | 23 | 1.7 |
| Comparative Example 13 | 0.50 | 100 | 23 | 0.6 |

3. Optimization of Air-Flow Rate in 5 L-Jar Culture

Example 14

(Pre-Pre Culture)

Colonies of *Comamonas testosteroni* NBRC 12047 strain were inoculated in a 3-mL pre-pre culture medium (LB Broth Miller Novagen catalog number: 71753-5CN)) prepared in eight 15-mL test tubes and cultured with shaking at a temperature of 30° C., at a rotation number of 230 rpm for 8 hours.

The pre-pre culture medium was prepared by dissolving LB Broth Miller Novagen (25 g) in water, diluting the mixture up to 1000 mL in a measuring flask, and sterilizing it with heat (121° C., 20 minutes)

(Pre-Culture)

The pre-pre-culture solution (3 mL) obtained was inoculated (added) in a 100-mL pre-culture medium (LB Broth Miller Novagen catalog number: 71753-5CN) prepared in eight 500 mL-flasks and cultured with shaking at a temperature 30° C. and a rotation number of 230 rpm for 16 hours.

The pre-pre-culture medium was prepared by dissolving LB Broth Miller Novagen (2.5 g) in water, diluting the mixture up to 100 mL in a measuring flask and sterilizing it with heat (121° C., 20 minutes)

(Main Culture)

The pre-culture solution (800 mL) obtained was concentrated by a centrifuge. Concentrated microbial cells were inoculated in a 2-L main-culture primary medium (sodium gluconate 10 g/L, dipotassium hydrogen phosphate 3.9 g/L ammonium sulfate 2.0 g/L, potassium dihydrogen phosphate dihydrate 2.1 g/L, EDTA 10.0 mg/L, magnesium chloride hexahydrate 100 mg/L, zinc sulfate heptahydrate 2.0 mg/L, iron sulfate heptahydrate 5.0 mg/L, manganese chloride tetrahydrate 10 mg/L, copper sulfate pentahydrate 0.2 mg/L, cobalt chloride hexahydrate 0.4 mg/L, ammonium molybdenum heptamolybdate tetrahydrate 0.2 mg/L, calcium chloride dihydrate 1.0 mg/L, LG-294 (1 g/L ADEKA CORPORATION)) prepared in a 5-L jar fermenter so as to obtain an initial $OD_{660}$ of 1.0, and cultured at a temperature 30° C. and a rotation number of 200 rpm, while aerating the medium with a gas containing 90% (v/v) of oxygen at a rate of 2.0 vvm and a pressure of 0.05 MPa, and controlling the lower limit of pH to be 6.95 and the upper limit of pH to be 7.05 (by use of a 1 N potassium sodium hydroxide solution).

The main-culture primary medium was prepared by mixing a solution, which is prepared by dissolving required amounts of sodium gluconate, dipotassium hydrogen phosphate, ammonium sulfate and potassium dihydrogen phosphate dihydrate in water, diluting the solution up to 2000 mL in a measuring flask and sterilizing it with heat (121° C., 20 minutes), and a solution of the other components (except sodium gluconate, dipotassium hydrogen phosphate, ammonium sulfate, potassium dihydrogen phosphate dihydrate), which was previously sterilized by a 0.20 μm-filter, in aseptic conditions.

(Addition of Feed Medium)

The main-culture feed medium (sodium gluconate 259 g/L, dipotassium hydrogen phosphate 1.12 g/L ammonium sulfate 1.12 g/L, potassium dihydrogen phosphate dihydrate 1.12 g/L, EDTA 0.02 mg/L, magnesium chloride hexahydrate 0.22 mg/L, zinc sulfate heptahydrate 0.22 mg/L, iron sulfate heptahydrate 0.22 mg/L) was added (fed) at a constant rate repeatedly at each time point when the dissolved oxygen started to rise again after 90-99% of the dissolved oxygen in the primary medium was consumed (pulse-feed method).

The main-culture feed medium was prepared by mixing a solution, which is prepared by dissolving sodium gluconate, dipotassium hydrogen phosphate, ammonium sulfate and potassium dihydrogen phosphate dihydrate in water, diluting the solution up to the above-described concentrations in a 1000 mL measuring flask and sterilizing it with heat (121° C., 20 minutes), and a solution of the other components (except sodium gluconate, dipotassium hydrogen phosphate, ammonium sulfate, potassium dihydrogen phosphate dihydrate), which was previously sterilized by a 0.20 μm-filter, in aseptic conditions.

Culture was carried out in total for 48 hours while taking a sample at appropriate times. The feed medium was added at a constant flow rate of 2.6 mL/min from the beginning of culture for about 48 hours. The pH of the culture was maintained at about 7.0 until the end of the culture. The culture solution obtained was measured for microbial density by measuring absorbance ($OD_{660}$) at 660 nm. The results are shown in Table 5.

Example 15

Culture was carried out in the same manner as in Example 14 except that the air-flow rate was controlled to be up to 0.5 vvm. The pH of the culture was maintained at about 7.0 until the end of the culture. The culture solution obtained was measured for microbial density in the same manner as in Example 1. The results are shown in Table 5.

Example 16

Culture was carried out in the same manner as in Example 14 except that the air-flow rate was controlled to be up to 1.0 vvm. The pH of the culture was maintained at about 7.0 until the end of the culture. The culture solution obtained was measured for microbial density in the same manner as in Example 1. The results are shown in Table 5.

TABLE 5

| | Air-flow rate (vvm) | Culture time (hr) | OD660 |
|---|---|---|---|
| Example 14 | 2 | 48 | 17.0 |
| Example 15 | 0.5 | 48 | 15.0 |
| Example 16 | 1 | 48 | 20.0 |

4. Optimization of Oxygen Concentration in Gas Aerated to 5-L Jar Culture

Example 17

(Pre-Pre Culture)

Colonies of *Comamonas testosteroni* NBRC 12047 strain were inoculated in a 3-mL pre-pre culture medium (LB Broth Miller Novagen catalog number: 71753-5CN)) prepared in eight 15-mL test tubes and cultured with shaking at a temperature of 30° C. and a rotation number of 230 rpm for 8 hours.

The pre-pre culture medium was prepared by dissolving LB Broth Miller Novagen (25 g) in water, diluting the mixture up to 1000 mL in a measuring flask, and sterilizing it with heat (121° C., 20 minutes)

(Pre-Culture)

The pre-pre-culture solution (3 mL) obtained was inoculated (added) in a 100-mL pre-culture medium (LB Broth Miller Novagen catalog number: 71753-5CN) prepared in eight 500 mL-flasks and cultured with shaking at a temperature 30° C. and a rotation number of 230 rpm for 16 hours.

The pre-pre-culture medium was prepared by dissolving LB Broth Miller Novagen (2.5 g) in water, diluting the mixture up to 100 mL in a measuring flask and sterilizing it with heat (121° C., 20 minutes)

(Main Culture)

The pre-culture solution obtained (800 mL) was concentrated by a centrifuge. Concentrated microbial cells were inoculated in a 2-L main-culture primary medium (sodium gluconate 10 g/L, dipotassium hydrogen phosphate 3.9 g/L ammonium sulfate 2.0 g/L, potassium dihydrogen phosphate dihydrate 2.1 g/L, EDTA 10.0 mg/L, magnesium chloride hexahydrate 100 mg/L, zinc sulfate heptahydrate 2.0 mg/L, iron sulfate heptahydrate 5.0 mg/L, manganese chloride tetrahydrate 10 mg/L, copper sulfate pentahydrate 0.2 mg/L, cobalt chloride hexahydrate 0.4 mg/L, ammonium molybdenum heptamolybdate tetrahydrate 0.2 mg/L, calcium chloride dihydrate 1.0 mg/L, LG-294 (1 g/L ADEKA CORPORATION)) prepared in a 5-L jar fermenter so as to obtain an initial $OD_{660}$ of 1.0, and cultured at a temperature 30° C. and a rotation number of 200 rpm, while aerating the medium with a gas containing 90% (v/v) or more of oxygen at a rate of 1.0 vvm and a pressure of 0.05 MPa, and controlling the lower limit of pH to be 6.95 and the upper limit of pH to be 7.05 (by use of a 1 N potassium sodium hydroxide solution).

The main-culture primary medium was prepared by mixing a solution, which is prepared by dissolving required amounts of sodium gluconate, dipotassium hydrogen phosphate, ammonium sulfate and potassium dihydrogen phosphate dihydrate in water, diluting the solution up to 2000 mL in a measuring flask and sterilizing it with heat (121° C., 20 minutes), and a solution of the other components (except sodium gluconate, dipotassium hydrogen phosphate, ammonium sulfate, potassium dihydrogen phosphate dihydrate), which was previously sterilized by a 0.20 μm-filter, in aseptic conditions.

(Addition of Feed Medium)

The main-culture feed medium (sodium gluconate 259 g/L, dipotassium hydrogen phosphate 1.12 g/L ammonium sulfate 1.12 g/L, potassium dihydrogen phosphate dihydrate 1.12 g/L, EDTA 0.02 mg/L, magnesium chloride hexahydrate 0.22 mg/L, zinc sulfate heptahydrate 0.22 mg/L, iron sulfate heptahydrate 0.22 mg/L) was added (fed) at a constant speed repeatedly at each time point when the dissolved oxygen started to rise again after 90-99% of the dissolved oxygen in the primary medium was consumed (pulse-feed method).

The main-culture feed medium was prepared by mixing a solution, which is prepared by dissolving required amounts of sodium gluconate, dipotassium hydrogen phosphate, ammonium sulfate and potassium dihydrogen phosphate dihydrate in water so as to be the concentration as mentioned above, and then diluting the solution up to 1000 mL in a measuring flask and sterilizing it with heat (121° C., 20 minutes), and a solution of the other components (except sodium gluconate, dipotassium hydrogen phosphate, ammonium sulfate, potassium dihydrogen phosphate dihydrate), which was previously sterilized by a 0.20 μm-filter, in aseptic conditions.

Culture was carried out in total for 25 hours while taking a sample at appropriate times. The feed medium was added at a constant flow rate of 2.6 mL/min from the beginning of culture for 48 hours. The pH of the culture was maintained at about 7.0 until the end of the culture. The culture solution obtained was measured for microbial density by measuring absorbance ($OD_{660}$) at 660 nm. The results are shown in Table 6.

Example 18

Culture was carried out in the same manner as in Example 17 except that aeration was carried out with a gas containing 20% (v/v) of oxygen at a rate of 1.0 vvm. The pH of the culture was maintained at about 7.0 until the end of culture. The culture solution obtained was measured for microbial density in the same manner as in Example 1. The results are shown in Table 6.

TABLE 6

| | Oxygen concentration of aeration gas (% v/v) | Culture time (hr) | OD660 |
|---|---|---|---|
| Example 17 | 90 or more | 25 | 24 |
| Example 18 | 20 | 25 | 15 |

5. Optimization of Addition Method in 5-L Jar

Example 19

(Pre-Pre Culture)

Colonies of *Comamonas testosteroni* NBRC 12047 strain were inoculated in a 3-mL pre-pre culture medium (LB Broth Miller Novagen catalog number: 71753-5CN) prepared in eight 15-mL test tubes and cultured with shaking at a temperature of 30° C. and a rotation number of 230 rpm for 8 hours.

The pre-pre culture medium was prepared by dissolving LB Broth Miller Novagen (25 g) in water, diluting the mixture up to 1000 mL in a measuring flask, and sterilizing it with heat (121° C., 20 minutes)

(Pre-Culture)

The pre-pre-culture solution (3 mL) obtained was inoculated (added) in a 100-mL pre-culture medium (LB Broth Miller Novagen catalog number: 71753-5CN) prepared in eight 500 mL-flasks and cultured with shaking at a temperature 30° C. and a rotation number of 230 rpm for 16 hours.

The pre-pre-culture medium was prepared by dissolving LB Broth Miller Novagen (2.5 g) in water, diluting the mixture up to 100 mL in a measuring flask and sterilizing it with heat (121° C., 20 minutes)

(Main Culture)

The resultant pre-culture solution (800 mL) was concentrated by a centrifuge. Concentrated microbial cells were inoculated in a 2-L main-culture primary medium (sodium gluconate 10 g/L, dipotassium hydrogen phosphate 3.9 g/L ammonium sulfate 2.0 g/L, potassium dihydrogen phosphate dihydrate 2.1 g/L, EDTA 10.0 mg/L, magnesium chloride hexahydrate 100 mg/L, zinc sulfate heptahydrate 2.0 mg/L, iron sulfate heptahydrate 5.0 mg/L, manganese chloride tetrahydrate 10 mg/L, copper sulfate pentahydrate 0.2 mg/L, cobalt chloride hexahydrate 0.4 mg/L, ammonium molybdenum heptamolybdate tetrahydrate 0.2 mg/L, calcium chloride dihydrate 1.0 mg/L, LG-294 (1 g/L ADEKA CORPORATION) prepared in a 5-L jar fermenter so as to obtain an initial $OD_{660}$ of 1.0, and cultured at a temperature 30° C. and a rotation number of 200 rpm, while aerating the medium with a gas containing 20% (v/v) or more of oxygen at a rate of 1.0 vvm and a pressure of 0.05 MPa, and controlling the lower limit of pH to be 6.95 and the upper limit of pH to be 7.05 (by use of a 1 N potassium sodium hydroxide solution).

The main-culture primary medium was prepared by mixing a solution, which is prepared by dissolving required amounts of sodium gluconate, dipotassium hydrogen phosphate, ammonium sulfate and potassium dihydrogen phosphate dihydrate in water, diluting the solution up to 2000 mL in a measuring flask and sterilizing it with heat (121° C., 20 minutes), and a solution of the other components (except sodium gluconate, dipotassium hydrogen phosphate, ammonium sulfate, potassium dihydrogen phosphate dihydrate), which was previously sterilized by a 0.20 μm-filter, in aseptic conditions.

(Addition of Feed Medium)

The main-culture feed medium (sodium gluconate 259 g/L, dipotassium hydrogen phosphate 1.12 g/L ammonium sulfate 1.12 g/L, potassium dihydrogen phosphate dihydrate 1.12 g/L, EDTA 0.02 mg/L, magnesium chloride hexahydrate 0.22 mg/L, zinc sulfate heptahydrate 0.22 mg/L, iron sulfate heptahydrate 0.22 mg/L) was added (fed) at a constant speed repeatedly at each time point when the dissolved oxygen started to rise again after 90-99% of the dissolved oxygen in the primary medium was consumed (pulse-feed method).

The main-culture primary medium was prepared by mixing a solution, which is prepared by dissolving required amounts of sodium gluconate, dipotassium hydrogen phosphate, ammonium sulfate and potassium dihydrogen phosphate dihydrate in water so as to be the concentration as mentioned above, and then diluting the solution up to 1000 mL in a measuring flask and sterilizing it with heat (121° C., 20 minutes), and a solution of the other components (except sodium gluconate, dipotassium hydrogen phosphate, ammonium sulfate, potassium dihydrogen phosphate dihydrate), which was previously sterilized by a 0.20 μm-filter, in aseptic conditions.

The pH of the culture was maintained at about 7.0 until the end of the culture. The culture solution obtained at the time of 48 hours of the culture was measured for microbial density by measuring absorbance ($OD_{660}$) at 660 nm. The amount of gluconic acid supplied (total of the amount of gluconic acid in primary medium and amount of gluconic acid in feed medium) was 80 g.

The yield of microbial cells vs. gluconic acid was calculated by dividing microbial density by the supply amount of gluconic acid. The results are shown in Table 7.

Example 20

Culture was carried out in the same manner as in Example 1 except that aeration was carried out with a gas containing 20% (v/v) of oxygen at a rate of 2 vvm; a feed medium was added at a constant rate of 0.1 mL/min; and culture was carried out up to 96 hours. The supply amount of gluconic acid was 136 g. The pH of the culture was maintained at about 7.0 until the end of culture. The culture solution obtained was measured for microbial density in the same manner as in Example 1. The results are shown in Table 7.

TABLE 7

| | Addition method | OD660 | Total addition amount of gluconic acid (g) | Yield (%) of microbial cells vs. gluconic acid |
|---|---|---|---|---|
| Example 19 | Pulse feed method | 28 | 136 | 42 |
| Example 20 | Continuous addition | 31 | 80 | 30 |

6. Method for Producing Lyophilized Bacteria

Example 21

A culture solution (5 mL) was placed in a 15 mL Falcon tube, and centrifuged to concentrate microbial cells 10 folds. To microbial cells (80 g-DCW/L) concentrated, trehalose serving as a cryoprotectant was added in the same weight as that of the microbial cells. The mixture was frozen by an ultracold freezer (CLN-50UW Nihon Freezer Co., Ltd.) at −80° C. for 17 hours. Lyophilization was carried out by a lyophilizer (FDU-2110 TOKYO RIKAKIKAI CO, LTD.) in the conditions: a degree of vacuum: 3.7 Pa, drying temperature: 30° C., drying time: 24 hr, and trap temperature: −45.5° C. The lyophilized microbial cells obtained were stored in a refrigerator for 40 days, and then, suspended in a 20 mM phosphate buffer. Evaluation of viable counts and a degradation test of a furan compound contained in wastewater were carried out as follows.

<Evaluation of Viable Counts>

The microbial cells lyophilized and stored at a refrigerator for 40 days were suspended in a 20 mM phosphate buffer and diluted 104 folds with the 20 mM phosphate buffer. The dilution solution (5 μl) was smeared onto an LB agar medium (LB Broth Miller Novagen catalog number: 71753-5CN, adjusted to contain 1.5% of an agar) and subjected to static culture at 30° C. for 2 days. The colonies emerged were visually counted and used as viable counts (CFU: colony forming unit).

<Degradation Test for Furan Compound Contained in Wastewater>

To 20 mL of MM liquid medium containing furfural whose concentration was adjusted to be 100 ppm and placed in a 200 mL-conical flask, *Comamonas testosteroni* NBRC12047 strain was added so as to obtain a final $OD_{660}$=0.1. The flask was closed with a cotton stopper and shaken at 30° C. and 230 rpm. Seventy two hours later, a sample was taken and a suspended matter in the sample was filtered by a 0.45 μm filter. The concentration of furfural in the sample was measured by HPLC.

Measurement conditions were as follows. Furfural was measured by use of a Nakalai 5C18-MS-II (4.6 ID×250 mm) column for 20 minutes by setting the ratio of 20 mM formic acid and methanol at 20:80. The results are shown in Table 8.

Example 22

The same procedure as in Example 21 was repeated except that trehalose 5 times as large as the weight of microbial cells was added. The results are shown in Table 8.

Example 23

The same procedure as in Example 21 was repeated except that the same amount (weight) of skim milk as that of microbial cells was added. The results are shown in Table 8.

Example 24

The same procedure as in Example 21 was repeated except that skim milk 5 times as large as the weight of microbial cells was added. The results are shown in Table 8.

Example 25

The same procedure as in Example 21 was repeated except that the same amount (weight) of sodium glutamate as that of microbial cells was added. The results are shown in Table 8.

Example 26

The same procedure as in Example 21 was repeated except that sodium glutamate 5 times as large as the weight of microbial cells was added. The results are shown in Table 8.

Comparative Example 14

Evaluation of viable counts and a degradation test for a furan compound in wastewater were carried out in the same manner as in Example 21 except that microbial cells centrifuged and concentrated 10 folds were not subjected to lyophilization. The results are shown in Table 8.

Comparative Example 15

Evaluation of viable counts and a degradation test for a furan compound contained in wastewater were carried out in the same manner as in Example 21 immediately after lyophilization except that a cryoprotectant was not added. The results are shown in Table 8.

TABLE 8

| | Lyophilization condition | Evaluation time | Vial counts (CFU) | Concentration of remaining furfural at 72 hours (mg/L) |
|---|---|---|---|---|
| Example 19 | Trehalose 1:1 | Lyophilized and then refrigerated for 40 days | 1812 | 0 |
| Example 20 | Trehalose 1:5 | Lyophilized and then refrigerated for 40 days | 2370 | 0 |
| Example 21 | Skim milk 1:1 | Lyophilized and then refrigerated for 40 days | 2104 | 0 |
| Example 22 | Skim milk 1:5 | Lyophilized and then refrigerated for 40 days | 1592 | 0 |
| Example 23 | Sodium glutamate 1:1 | Lyophilized and then refrigerated for 40 days | 1704 | 0 |
| Example 24 | Sodium glutamate 1:5 | Lyophilized and then refrigerated for 40 days | 2896 | 0 |
| Comparative Example 14 | Before lyophilization | — | 1680 | 0 |
| Comparative Example 15 | No cryoprotectant | After lyophilization | 0 | — |

INDUSTRIAL APPLICABILITY

According to the present invention, there is provided a biological treatment of wastewater containing a furan compound, in which a furan compound, acid components and sugars in wastewater can be efficiently removed while preventing a reduction of the treatment capacity. The treated water obtained by the present invention has a high quality (CODcr: 500 ppm or less) and can satisfy strict regulations on wastewater.

All publications, patents and patent applications cited in the specification are incorporated herein as their entireties by reference.

The invention claimed is:

1. A method for treating wastewater, comprising contacting wastewater containing a furan compound with at least one selected from the group consisting of: a microorganism belonging to the genus *Comamonas*; a microorganism belonging to the genus *Burkholderia*; and a microorganism belonging to the genus *Paraburkholderia,* wherein the microorganism belonging to the genus *Comamonas* is *Comamonas testosteroni* and/or *Comamonas thiooxydans*; the microorganism belonging to the genus *Burkholderia* is *Burkholderia multivorans*; the microorganism belonging to the genus *Paraburkholderia* is *Paraburkholderia xenovorans.*

2. The method for treating wastewater according to claim 1, wherein the furan compound comprises a furan-aldehyde.

3. The method for treating wastewater according to claim 1, further comprising contacting the wastewater with at least one selected from the group consisting of activated carbon, Fenton's catalyst and a polycyclic aromatic degrading enzyme.

4. The method for treating wastewater according to claim 1, wherein wastewater obtained by the treating wastewater has a CODcr value of 500 ppm or less.

5. A method for treating wastewater, comprising contacting wastewater containing a furan compound with at least one selected from the group consisting of: a microorganism belonging to the genus *Comamonas*, a microorganism belonging to the genus *Burkholderia*, and a microorganism belonging to the genus *Paraburkholderia,* wherein the microorganism belonging to the genus *Comamonas* is *Comamonas testosteroni* and/or *Comamonas thiooxydans*; the microorganism belonging to the genus *Burkholderia* is *Burkholderia multivorans*; the microorganism belonging to the genus *Paraburkholderia* is *Paraburkholderia xenovorans*, and the contacting comprises contacting the wastewater and the at least one microorganism in the presence of a membrane separator.

6. A method for culturing a microorganism belonging to the genus *Comamonas*, or a microorganism belonging to the genus *Paraburkholderia*, the method comprising culturing the microorganism in a culture medium comprising gluconic acid wherein the culture medium comprising the microorganism has an optical density of 15 or more at a wavelength of 660 nm, 24 hours after initiation of culture.

7. The method according to claim 6, wherein the culture medium comprising the microorganism has an optical density of 20 or more at a wavelength of 660 nm, 48 hours after the initiation of culture.

8. The method according to claim 6, wherein a concentration of the gluconic acid in the culture medium is 10 g/L or less.

9. The method according to claim 6, wherein the culture is carried out with a semi-batch culture or a fed-batch culture.

10. The method according to claim 6, comprising a step of passing a gas comprising 90% (v/v) or more of oxygen through the culture medium.

11. The method according to claim 10, wherein the gas is passed at a rate of 6 to 5 vvm.

12. A method for culturing a microorganism belonging to the genus *Comamonas*, a microorganism belonging to the genus *Burkholderia* or a microorganism belonging to the genus *Paraburkholderia*, comprising a step of culturing the microorganism in a culture medium comprising gluconic acid, wherein the microorganism has a proliferation rate of 0.2 g/L/hr or more on a basis of dry weight of microbial cells.

* * * * *